United States Patent
Ihara et al.

(10) Patent No.: US 9,045,525 B2
(45) Date of Patent: Jun. 2, 2015

(54) AMYLOID β-PROTEIN-SPECIFIC PRODUCTION-INHIBITING POLYPEPTIDE

(71) Applicant: THE DOSHISHA, Kyoto-shi, Kyoto (JP)

(72) Inventors: Yasuo Ihara, Kyotanabe (JP); Satoru Funamoto, Kyotanabe (JP); Toru Sasaki, Tokyo (JP)

(73) Assignee: THE DOSHISHA, Kyoto (JP)

( * ) Notice: Subject to any disclaimer, the term of this patent is extended or adjusted under 35 U.S.C. 154(b) by 0 days.

(21) Appl. No.: 14/372,597

(22) PCT Filed: Jan. 16, 2013

(86) PCT No.: PCT/JP2013/050663
§ 371 (c)(1),
(2) Date: Jul. 16, 2014

(87) PCT Pub. No.: WO2013/108780
PCT Pub. Date: Jul. 25, 2013

(65) Prior Publication Data
US 2014/0371152 A1    Dec. 18, 2014

(30) Foreign Application Priority Data

Jan. 17, 2012  (JP) ................................. 2012-006687
Sep. 21, 2012  (JP) ................................. 2012-208277

(51) Int. Cl.
| | |
|---|---|
| C07K 7/08 | (2006.01) |
| C07K 4/00 | (2006.01) |
| C07K 14/00 | (2006.01) |
| A61P 25/28 | (2006.01) |
| C07K 7/06 | (2006.01) |
| C07K 14/81 | (2006.01) |

(Continued)

(52) U.S. Cl.
CPC . *C07K 7/06* (2013.01); *C07K 14/81* (2013.01); *C07K 14/8142* (2013.01); *C07K 14/4711* (2013.01); *A61K 38/00* (2013.01); *C07K 14/00* (2013.01)

(58) Field of Classification Search
None
See application file for complete search history.

(56) References Cited

U.S. PATENT DOCUMENTS

2009/0176711 A1    7/2009   Chae et al.

FOREIGN PATENT DOCUMENTS

WO       2009/068269        6/2009

OTHER PUBLICATIONS

Funamoto et al. Substrate ectodomain is critical for substrate preference and inhibition of gamma-secretase. Nature Communications | 4:2529, 2013, 1-12.*

(Continued)

*Primary Examiner* — Gregory S Emch
*Assistant Examiner* — Aurora M Fontainhas
(74) *Attorney, Agent, or Firm* — Roylance, Abrams, Berdo & Goodman, LLP

(57) ABSTRACT

A primary object of the present invention is to develop a compound that specifically inhibits the production of Aβ protein and serves as an active ingredient of a drug to treat and/or prevent Alzheimer's disease.
This object can be achieved by a polypeptide having the amino acid sequence represented by any one of SEQ ID NOs: 1, 13, 14, and 22, that binds to the N-terminal region of βCTF; a γ-secretase activity inhibitor containing the polypeptide; β-secretase activity inhibitor; Aβ protein production inhibitor; and an agent for treating and/or preventing Alzheimer's disease.

15 Claims, 13 Drawing Sheets

(51) Int. Cl.
    *C07K 14/47*    (2006.01)
    *A61K 38/00*    (2006.01)

(56) References Cited

OTHER PUBLICATIONS

Shah, S. et al., Nicastrin Functions as a gamma-Secretase-Substrate Receptor, Cell, 2005, vol. 122, pp. 435-447.

Wong, G. et al., Chronic Treatment with the gamma-Secretase Inhibitor LY-411,575 Inhibits beta-Amyloid Peptide Production and Alters Lymphopoiesis and Intestinal Cell Differentiation, The Journal of Biological Chemistry, 2004, vol. 279, No. 13, pp. 12876-12882.

Choi, S.E. et al., Moderate Reduction of gamma-Secretase: Is There a Therapeutic Sweet Spot?, The Journal of Neuroscience, 2007, vol. 27, No. 50, pp. 13579-13580.

Page, R. et al., Generation of A-beta38 and A-beta42 Is Independently and Differentially Affected by Familial Alzheimer Disease— associated Presenilin Mutations and gamma-Secretase Modulation, The Journal of Biological Chemistry, 2008, vol. 283, No. 2, pp. 677-683.

Kakuda, N. et al., Altered gamma-secretase activity in mild cognitive impairment and Alzheimer's disease, EMBO Molecular Medicine, 2012, vol. 4, pp. 344-352.

International Search Report for PCT/JP2013/050663, dated Feb. 12, 2013.

* cited by examiner

SEQUENCE LISTING

```
<160> NUMBER OF SEQ ID NOS: 23

<210> SEQ ID NO 1
<211> LENGTH: 23
<212> TYPE: PRT
<213> ORGANISM: Artificial
<220> FEATURE:
<223> OTHER INFORMATION: polypeptide
<220> FEATURE:
<221> NAME/KEY: MISC_FEATURE
<222> LOCATION: (2)..(2)
<223> OTHER INFORMATION: X is Asn, Ser, Asp, Gly, His, Val, Leu, Arg,
      or Phe.
<220> FEATURE:
<221> NAME/KEY: MISC_FEATURE
<222> LOCATION: (3)..(3)
<223> OTHER INFORMATION: X is Thr, Ile, Leu, Pro, Tyr, or Arg.
<220> FEATURE:
<221> NAME/KEY: MISC_FEATURE
<222> LOCATION: (4)..(4)
<223> OTHER INFORMATION: X is Leu, Arg, Val, Ile, Thr, Phe, or Ser.
<220> FEATURE:
<221> NAME/KEY: MISC_FEATURE
<222> LOCATION: (5)..(5)
<223> OTHER INFORMATION: X is Ile, Val, Ser, Asp, Asn, or Thr.
<220> FEATURE:
<221> NAME/KEY: MISC_FEATURE
<222> LOCATION: (5)..(5)
<223> OTHER INFORMATION: X is Ile, Val, Ser, Asp, Asn, or Thr.
<220> FEATURE:
<221> NAME/KEY: MISC_FEATURE
<222> LOCATION: (11)..(11)
<223> OTHER INFORMATION: X is Ser, His, Asp, Thr, Phe, Tyr, Ile, or Ala.
<220> FEATURE:
<221> NAME/KEY: MISC_FEATURE
<222> LOCATION: (12)..(12)
<223> OTHER INFORMATION: X is Leu, Gly, Asn, Ser, Thr, Ala, Arg, or Tyr.
<220> FEATURE:
<221> NAME/KEY: MISC_FEATURE
<222> LOCATION: (13)..(13)
<223> OTHER INFORMATION: X is Thr, Asp, Tyr, Ser, Phe, His, or Asn.
```

```
<220> FEATURE:
<221> NAME/KEY: MISC_FEATURE
<222> LOCATION: (14)..(14)
<223> OTHER INFORMATION: X is Arg, Leu, Val, Ala, Ile, Ser, or Tyr.
<220> FEATURE:
<221> NAME/KEY: MISC_FEATURE
<222> LOCATION: (16)..(16)
<223> OTHER INFORMATION: X is Phe or Tyr.
<220> FEATURE:
<221> NAME/KEY: MISC_FEATURE
<222> LOCATION: (19)..(19)
<223> OTHER INFORMATION: X is Ser, Phe, or Tyr.
<220> FEATURE:
<221> NAME/KEY: MISC_FEATURE
<222> LOCATION: (21)..(21)
<223> OTHER INFORMATION: X is Val, Ile, Ser, Thr, Tyr, Gly, His, or Arg.
<220> FEATURE:
<221> NAME/KEY: MISC_FEATURE
<222> LOCATION: (22)..(22)
<223> OTHER INFORMATION: X is Asp, Asn, His, Pro, Ile, Arg, or Ser.
<220> FEATURE:
<221> NAME/KEY: MISC_FEATURE
<222> LOCATION: (23)..(23)
<223> OTHER INFORMATION: X is Ser, Val, Phe, Asn, Thr, Tyr, His, Ile,
      Arg, or Asp.

<400> SEQUENCE: 1

Met Xaa Xaa Xaa Xaa Cys Asp Cys Tyr Cys Xaa Xaa Xaa Xaa Cys Xaa
1               5                   10                  15

Cys Tyr Xaa Cys Xaa Xaa Xaa
            20

<210> SEQ ID NO 2
<211> LENGTH: 23
<212> TYPE: PRT
<213> ORGANISM: Artificial
<220> FEATURE:
<223> OTHER INFORMATION: 9-7

<400> SEQUENCE: 2

Met Asn Thr Leu Ile Cys Asp Cys Tyr Cys Ser Leu Thr Arg Cys Phe
1               5                   10                  15

Cys Tyr Ser Cys Val Asp Ser
            20

<210> SEQ ID NO 3
<211> LENGTH: 23
<212> TYPE: PRT
<213> ORGANISM: Artificial
<220> FEATURE:
<223> OTHER INFORMATION: #1 polypeptide

<400> SEQUENCE: 3

Met Ser Ile Arg Val Cys Asp Cys Tyr Cys His Gly Asp Leu Cys Phe
1               5                   10                  15

Cys Tyr Ser Cys Ile Asn Ser
            20

<210> SEQ ID NO 4
<211> LENGTH: 23
<212> TYPE: PRT
<213> ORGANISM: Artificial
<220> FEATURE:
<223> OTHER INFORMATION: #2 polypeptide
```

```
<400> SEQUENCE: 4

Met Asp Thr Val Ile Cys Asp Cys Tyr Cys Asp Asn Tyr Val Cys Phe
1               5                   10                  15

Cys Tyr Ser Cys Ser His Val
            20

<210> SEQ ID NO 5
<211> LENGTH: 23
<212> TYPE: PRT
<213> ORGANISM: Artificial
<220> FEATURE:
<223> OTHER INFORMATION: #3 polypeptide

<400> SEQUENCE: 5

Met Gly Leu Ile Ser Cys Asp Cys Tyr Cys Asp Ser Thr Ala Cys Phe
1               5                   10                  15

Cys Tyr Ser Cys Thr Asp Phe
            20

<210> SEQ ID NO 6
<211> LENGTH: 23
<212> TYPE: PRT
<213> ORGANISM: Artificial
<220> FEATURE:
<223> OTHER INFORMATION: #4 polypeptide

<400> SEQUENCE: 6

Met His Leu Val Ile Cys Asp Cys Tyr Cys Thr Thr Asp Ile Cys Tyr
1               5                   10                  15

Cys Tyr Ser Cys Thr Pro Asn
            20

<210> SEQ ID NO 7
<211> LENGTH: 23
<212> TYPE: PRT
<213> ORGANISM: Artificial
<220> FEATURE:
<223> OTHER INFORMATION: #5 Polypeptide

<400> SEQUENCE: 7

Met Val Pro Val Val Cys Asp Cys Tyr Cys Phe Leu Ser Val Cys Phe
1               5                   10                  15

Cys Tyr Ser Cys Tyr Ile Thr
            20

<210> SEQ ID NO 8
<211> LENGTH: 23
<212> TYPE: PRT
<213> ORGANISM: Artificial
<220> FEATURE:
<223> OTHER INFORMATION: #6 polypeptide

<400> SEQUENCE: 8

Met Leu Tyr Thr Ser Cys Asp Cys Tyr Cys Asp Ala Phe Ser Cys Phe
1               5                   10                  15

Cys Tyr Ser Cys Gly Pro Tyr
            20

<210> SEQ ID NO 9
<211> LENGTH: 23
<212> TYPE: PRT
<213> ORGANISM: Artificial
<220> FEATURE:
<223> OTHER INFORMATION: #7 polypeptide
```

-continued

<400> SEQUENCE: 9

Met Arg Ile Phe Asp Cys Asp Cys Tyr Cys Tyr Arg Asp Ile Cys Tyr
1               5                   10                  15

Cys Tyr Phe Cys Thr Arg His
            20

<210> SEQ ID NO 10
<211> LENGTH: 23
<212> TYPE: PRT
<213> ORGANISM: Artificial
<220> FEATURE:
<223> OTHER INFORMATION: #8 polypeptide

<400> SEQUENCE: 10

Met Gly Arg Val Asn Cys Asp Cys Tyr Cys Ile Gly His Tyr Cys Tyr
1               5                   10                  15

Cys Tyr Tyr Cys His Asn Ile
            20

<210> SEQ ID NO 11
<211> LENGTH: 23
<212> TYPE: PRT
<213> ORGANISM: Artificial
<220> FEATURE:
<223> OTHER INFORMATION: #9 polypeptide

<400> SEQUENCE: 11

Met Pro Leu Ser Ile Cys Asp Cys Tyr Cys Ile Ser Thr Ile Cys Tyr
1               5                   10                  15

Cys Tyr Phe Cys Val His Arg
            20

<210> SEQ ID NO 12
<211> LENGTH: 23
<212> TYPE: PRT
<213> ORGANISM: Artificial
<220> FEATURE:
<223> OTHER INFORMATION: #10 polypeptide

<400> SEQUENCE: 12

Met Pro Thr Val Tyr Cys Asp Cys Tyr Cys Ala Tyr Asn Ala Cys Tyr
1               5                   10                  15

Cys Tyr Tyr Cys Arg Ser Asp
            20

<210> SEQ ID NO 13
<211> LENGTH: 21
<212> TYPE: PRT
<213> ORGANISM: Artificial
<220> FEATURE:
<223> OTHER INFORMATION: 6-5

<400> SEQUENCE: 13

Met His His Val Tyr Cys Asp Cys Tyr Cys Phe Gly Pro Val Cys Tyr
1               5                   10                  15

Cys His Ser Cys Thr
            20

<210> SEQ ID NO 14
<211> LENGTH: 11
<212> TYPE: PRT
<213> ORGANISM: Artificial
<220> FEATURE:
<223> OTHER INFORMATION: S4 polypeptide

```
<220> FEATURE:
<221> NAME/KEY: MISC_FEATURE
<222> LOCATION: (3)..(3)
<223> OTHER INFORMATION: X is L-4,4'-Biphenylalanine.

<400> SEQUENCE: 14

Phe Arg Xaa Gly Trp Val Tyr Thr Tyr Thr Val
 1               5                  10

<210> SEQ ID NO 15
<211> LENGTH: 28
<212> TYPE: PRT
<213> ORGANISM: Artificial
<220> FEATURE:
<223> OTHER INFORMATION: Amyloid beta 1-28

<400> SEQUENCE: 15

Asp Ala Glu Phe Arg His Asp Ser Gly Tyr Glu Val His His Gln Lys
 1               5                  10                  15

Leu Val Phe Phe Ala Glu Asp Val Gly Ser Asn Lys
            20                  25

<210> SEQ ID NO 16
<211> LENGTH: 107
<212> TYPE: PRT
<213> ORGANISM: Artificial
<220> FEATURE:
<223> OTHER INFORMATION: C99-FLAG

<400> SEQUENCE: 16

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr Val Ile Val Ile Thr
        35                  40                  45

Leu Val Met Leu Lys Lys Lys Gln Tyr Thr Ser Ile His His Gly Val
    50                  55                  60

Val Glu Val Asp Ala Ala Val Thr Pro Glu Glu Arg His Leu Ser Lys
65                  70                  75                  80

Met Gln Gln Asn Gly Tyr Glu Asn Pro Thr Tyr Lys Phe Phe Glu Gln
                85                  90                  95

Met Gln Asn Asp Tyr Lys Asp Asp Asp Lys
            100                 105

<210> SEQ ID NO 17
<211> LENGTH: 628
<212> TYPE: PRT
<213> ORGANISM: Artificial
<220> FEATURE:
<223> OTHER INFORMATION: Modefied Notch protein

<400> SEQUENCE: 17

Met Pro Arg Leu Leu Thr Pro Leu Leu Cys Leu Thr Leu Leu Pro Ala
 1               5                  10                  15

Leu Ala Ala Arg Gly Leu Arg Ile Asp Ser Asn Ser Arg Ile Pro Tyr
            20                  25                  30

Lys Ile Glu Ala Val Lys Ser Glu Pro Val Glu Pro Pro Leu Pro Ser
        35                  40                  45

Gln Leu His Leu Met Tyr Val Ala Ala Ala Ala Phe Val Leu Leu Phe
    50                  55                  60
```

```
Phe Val Gly Cys Gly Val Leu Leu Ser Arg Lys Arg Arg Gln His
 65                  70                  75                  80

Gly Gln Leu Trp Phe Pro Glu Gly Phe Lys Val Ser Glu Ala Ser Lys
                 85                  90                  95

Lys Lys Arg Arg Glu Pro Leu Gly Glu Asp Ser Val Gly Leu Lys Pro
            100                 105                 110

Leu Lys Asn Ala Ser Asp Gly Ala Leu Met Asp Asp Asn Gln Asn Glu
            115                 120                 125

Trp Gly Asp Glu Asp Leu Glu Thr Lys Lys Phe Arg Phe Glu Glu Pro
    130                 135                 140

Val Val Leu Pro Asp Leu Ser Asp Gln Thr Asp His Arg Gln Trp Thr
145                 150                 155                 160

Gln Gln His Leu Asp Ala Ala Asp Leu Arg Met Ser Ala Met Ala Pro
                165                 170                 175

Thr Pro Pro Gln Gly Glu Val Asp Ala Asp Cys Met Asp Val Asn Val
            180                 185                 190

Arg Gly Pro Asp Gly Phe Thr Pro Leu Met Ile Ala Ser Cys Ser Gly
            195                 200                 205

Gly Gly Leu Glu Thr Gly Asn Ser Glu Glu Glu Asp Ala Pro Ala
    210                 215                 220

Val Ile Ser Asp Phe Ile Tyr Gln Gly Ala Ser Leu His Asn Gln Thr
225                 230                 235                 240

Asp Arg Thr Gly Glu Thr Ala Leu His Leu Ala Ala Arg Tyr Ser Arg
                245                 250                 255

Ser Asp Ala Ala Lys Arg Leu Leu Glu Ala Ser Ala Asp Ala Asn Ile
            260                 265                 270

Gln Asp Asn Met Gly Arg Thr Pro Leu His Ala Ala Val Ser Ala Asp
            275                 280                 285

Ala Gln Gly Val Phe Gln Ile Leu Leu Arg Asn Arg Ala Thr Asp Leu
    290                 295                 300

Asp Ala Arg Met His Asp Gly Thr Thr Pro Leu Ile Leu Ala Ala Arg
305                 310                 315                 320

Leu Ala Leu Glu Gly Met Leu Glu Asp Leu Ile Asn Ser His Ala Asp
                325                 330                 335

Val Asn Ala Val Asp Asp Leu Gly Lys Ser Ala Leu His Trp Ala Ala
            340                 345                 350

Ala Val Asn Asn Val Asp Ala Ala Val Val Leu Leu Lys Asn Gly Ala
            355                 360                 365

Asn Lys Asp Met Gln Asn Asn Lys Glu Glu Thr Pro Leu Phe Leu Ala
    370                 375                 380

Ala Arg Glu Gly Ser Tyr Glu Thr Ala Lys Val Leu Leu Asp His Phe
385                 390                 395                 400

Ala Asn Arg Asp Ile Thr Asp His Met Asp Arg Leu Pro Arg Asp Ile
                405                 410                 415

Ala Gln Glu Arg Met His His Asp Ile Val Arg Leu Leu Asp Glu Tyr
            420                 425                 430

Asn Leu Val Arg Ser Pro Gln Leu His Gly Thr Ala Leu Gly Gly Thr
    435                 440                 445

Pro Thr Leu Ser Pro Thr Leu Cys Ser Pro Asn Gly Tyr Leu Gly Asn
450                 455                 460

Leu Lys Ser Ala Thr Gln Gly Lys Lys Ala Arg Lys Pro Ser Thr Lys
465                 470                 475                 480
```

```
Gly Leu Ala Cys Gly Ser Lys Glu Ala Lys Asp Leu Lys Ala Arg Arg
                485                 490                 495
Lys Lys Ser Gln Asp Gly Lys Gly Cys Leu Leu Asp Ser Ser Met Thr
            500                 505                 510
Arg His Arg Gly Arg Arg Tyr Arg Phe Lys Ala Met Glu Gln Lys Leu
            515                 520                 525
Ile Ser Glu Glu Asp Leu Asn Glu Met Glu Gln Lys Leu Ile Ser Glu
            530                 535                 540
Glu Asp Leu Asn Glu Met Glu Gln Lys Leu Ile Ser Glu Glu Asp Leu
545                 550                 555                 560
Asn Glu Met Glu Gln Lys Leu Ile Ser Glu Glu Asp Leu Asn Glu Met
                565                 570                 575
Glu Gln Lys Leu Ile Ser Glu Glu Asp Leu Asn Glu Met Glu Ser Leu
            580                 585                 590
Gly Asp Leu Thr Met Glu Gln Lys Leu Ile Ser Glu Glu Asp Leu Asn
            595                 600                 605
Ser Cys Ser Pro Gly Asp Pro Leu Val Leu Glu Leu Asp Tyr Lys Asp
            610                 615                 620
Asp Asp Asp Lys
625

<210> SEQ ID NO 18
<211> LENGTH: 72
<212> TYPE: PRT
<213> ORGANISM: Artificial
<220> FEATURE:
<223> OTHER INFORMATION: APP-EQ-FLAG

<400> SEQUENCE: 18

Met Glu Gln Lys Leu Ile Ser Glu Glu Asp Leu Thr Arg Pro Gly Ser
1               5                   10                  15
Gly Leu Thr Asn Ile Lys Thr Glu Glu Ile Ser Glu Val Lys Met Asp
            20                  25                  30
Ala Glu Phe Arg His Asp Ser Gly Tyr Glu Val His His Gln Lys Leu
            35                  40                  45
Val Phe Phe Ala Glu Asp Val Gly Ser Asn Lys Gly Ala Ile Ile Gly
        50                  55                  60
Asp Tyr Lys Asp Asp Asp Asp Lys
65                  70

<210> SEQ ID NO 19
<211> LENGTH: 23
<212> TYPE: PRT
<213> ORGANISM: Artificial
<220> FEATURE:
<223> OTHER INFORMATION: #4 polypeptide rev

<400> SEQUENCE: 19

Asn Pro Thr Cys Ser Tyr Cys Tyr Cys Ile Asp Thr Thr Cys Tyr Cys
1               5                   10                  15
Asp Cys Ile Val Leu His Met
            20

<210> SEQ ID NO 20
<211> LENGTH: 99
<212> TYPE: PRT
<213> ORGANISM: Homo sapiens
```

<400> SEQUENCE: 20

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr Val Ile Val Ile Thr
        35                  40                  45

Leu Val Met Leu Lys Lys Lys Gln Tyr Thr Ser Ile His His Gly Val
    50                  55                  60

Val Glu Val Asp Ala Ala Val Thr Pro Glu Glu Arg His Leu Ser Lys
65                  70                  75                  80

Met Gln Gln Asn Gly Tyr Glu Asn Pro Thr Tyr Lys Phe Phe Glu Gln
                85                  90                  95

Met Gln Asn

<210> SEQ ID NO 21
<211> LENGTH: 99
<212> TYPE: PRT
<213> ORGANISM: Mus musculus

<400> SEQUENCE: 21

Asp Ala Glu Phe Gly His Asp Ser Gly Phe Glu Val Arg His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr Val Ile Val Ile Thr
        35                  40                  45

Leu Val Met Leu Lys Lys Lys Gln Tyr Thr Ser Ile His His Gly Val
    50                  55                  60

Val Glu Val Asp Ala Ala Val Thr Pro Glu Glu Arg His Leu Ser Lys
65                  70                  75                  80

Met Gln Gln Asn Gly Tyr Glu Asn Pro Thr Tyr Lys Phe Phe Glu Gln
                85                  90                  95

Met Gln Asn

<210> SEQ ID NO 22
<211> LENGTH: 11
<212> TYPE: PRT
<213> ORGANISM: Artificial
<220> FEATURE:
<223> OTHER INFORMATION: S2 polypeptide
<220> FEATURE:
<221> NAME/KEY: MISC_FEATURE
<222> LOCATION: (3)..(3)
<223> OTHER INFORMATION: X is L-4,4'-Biphenylalanine.

<400> SEQUENCE: 22

Phe Arg Xaa Gly Trp Val Tyr Thr Tyr Thr Val
1               5                   10

<210> SEQ ID NO 23
<211> LENGTH: 21
<212> TYPE: PRT
<213> ORGANISM: Artificial
<220> FEATURE:
<223> OTHER INFORMATION: L13 polypeptide

```
<400> SEQUENCE: 23

Met Leu Ile Cys Asp Cys Tyr Cys Asp Pro Arg Ser Cys Ile Cys Gly
1               5                   10                  15

Ser Cys Thr Leu Val
            20
```

AMYLOID β-PROTEIN-SPECIFIC PRODUCTION-INHIBITING POLYPEPTIDE

TECHNICAL FIELD

The present invention relates to a polypeptide that particularly inhibits the production of amyloid β protein.

BACKGROUND ART

The amyloid β protein ("Aβ protein") is considered to be one of the proteins that cause Alzheimer's disease. Particularly, the accumulation of the Aβ protein in the brain is recognized as one of the pathological hallmarks of Alzheimer's disease. Accumulation of Aβ protein in the brain forms a rigid fibrous molecular structure. It is believed that this causes the death of neurons in the brain, damaging neural function and, as a result, causing the onset of Alzheimer's disease.

Aβ protein is formed in such a manner that an amyloid precursor protein (or "APP"), which is a transmembrane protein, is cleaved by β-secretase to form βCTF, which is also a transmembrane protein, and the βCTF is further cleaved by γ-secretase to form the Aβ protein. The Aβ protein thus formed is believed to be released from the cell membrane and accumulate in the brain.

It is known that the βCTF cleaved by γ-secretase is divided into Aβ protein and AICD, and it is also known that sAPPβ is released when the APP is cleaved by β-secretase (FIG. 1).

Based on the matured APP, Aβ protein corresponds to the 653rd to 694th amino acid residues, and βCTF corresponds to the 653rd to 751st amino acid residues. The sAPPβ corresponds to the 18th to 652nd amino acid residues and AICD corresponds to the 701st to 751st amino acid residues.

For the reasons described above, a γ-secretase inhibitor was believed to be effective in inhibiting the accumulation of Aβ protein, which is a protein that causes Alzheimer's disease.

However, γ-secretase, which is known as a complex comprising Pen-2, presenilin, nicastrin, and Aph-1 each being a transmembrane protein, is a aspartic protease that recognizes, as the substrate, not only the APP mentioned above but also transmembrane proteins, such as APLP1, APLP2, Notch, Jagged2, Delta1, E-cadherin, N-cadherin, CD44, ErbB4, Nectin1, and LRP1; receptors; etc.

Accordingly, if L-685,458, DAPT, LY-411,575, and like γ-secretase inhibitors are used to inhibit the production of Aβ protein, the enzyme activity of γ-secretase as a protease against the proteins other than βCTF will also be inhibited; therefore, use of such an inhibitor without modification as a drug may cause undesirable side effects.

For example, it has been reported that LY-411,575, which is one of the γ-secretase inhibitors, induces atrophy of the thymus and reduces the number of mature B cells in the spleen. If such an inhibitor is used as a pharmaceutical composition without modification, there is a risk that this may trigger side effects in immunity, etc. (NPL 1). Furthermore, it has been reported that lowering the enzyme activity of γ-secretase itself may cause skin abnormalities, squamous cancer, spleen hypertrophy, and the like (NPL 2).

Considering the production mechanism of Aβ protein, use of a compound that inhibits the enzyme activity of β-secretase also may be effective. However, there is a report that such use will decrease the number of births of β-secretase knockout mice; therefore, use of such a compound as a drug for Alzheimer's disease is not preferable.

There are findings that nonsteroidal anti-inflammatory drugs (or "NSAIDs") are effective in inhibiting the production of Aβ protein. However, it is also known that these drugs are not effective for some familial Alzheimer's diseases (e.g., those associated presenilin mutations) (NPL 3). Furthermore, γ-secretase isolated from patients with mild cognitive impairment or Alzheimer's disease exhibits change in its activity, indicating that the effect of the γ-secretase modulator that reduces the production of Aβ42 is low (NPL 4).

γ-Secretase-dependent cleavage of βCTF fused with FLAG tag at the N-terminus is not observed in the presence of anti-FLAG antibody (Non-patent Literature 5).

CITATION LIST

Non-Patent Literature

NPL 1: Wong, G. T. et al., J. Biol. Chem. 2004; 279: 12876-12882
NPL 2: Choi, S. H. et al., J. Neurosci. 2007; 27: 13579-13580
NPL 3: Page, R. M. et al., J. Biol. Chem. 2008; 283: 677-683
NPL 4: Kakuda, N. et al., EMBO Mol. Med. 2012; 4: 344-352
NPL 5: Shah, S. et al., Cell. 2005; 122: 435-447

SUMMARY OF INVENTION

Technical Problem

As described above, the development of a compound that inhibits accumulation of Aβ protein has been in demand for the treatment and/or prevention of Alzheimer's disease; however, there is no finding so far relating to a compound that particularly inhibits the production of Aβ protein.

The main purpose of this invention is to develop a compound that particularly inhibits the production of Aβ protein and serves as an active ingredient of a medicament for use in the treatment and/or prevention of Alzheimer's disease.

Solution to Problem

In seeking a compound that particularly inhibits the production of Aβ protein, the present inventors have focused on the fact that Aβ protein is produced by the enzyme activity of γ-secretase against βCTF. Therefore, the inventors searched for a compound that achieves the effect of particularly inhibiting the production of Aβ protein not in view of inhibiting the enzyme activity of γ-secretase itself but in view of particularly inhibiting the binding of γ-secretase and βCTF.

The inventors found that by reacting βCTF with γ-secretase in the presence of a monoclonal antibody that particularly binds to the N-terminal region, which is the extracellular region of βCTF, the effect for remarkably and particularly inhibiting the production of Aβ protein can be achieved. The inventors also found that little effect is made on the enzyme activity of the γ-secretase to substrates other than βCTF.

The inventors conducted extensive research based on the above and found that a peptide having a specific amino acid sequence exhibits remarkable effects as a compound that particularly inhibits the production of Aβ protein. The present invention encompasses the wide range of embodiments described below.

Item 1. A polypeptide having the amino acid sequence represented by any one of SEQ ID NOs: 1, 13, 14, and 22, the polypeptide binding to the N-terminal region of βCTF.

Particularly, the examples of the inventions include the embodiments described in Item 1-1 to Item 1-6 below.

Item 1-1. The polypeptide according to Item 1, which has the amino acid sequence represented by any one of SEQ ID NOs: 2-14 and 22.

Item 1-3. The polypeptide according to Item 1, which has the amino acid sequence represented by any one of SEQ ID NOs: 3, 4, 6, 10, 11, 14, and 22.

Item 1-4. The polypeptide according to any one of Item 1 and Items (1-1) to (1-3), wherein the amide terminal is acetylated and/or the carboxy terminal is amidated.

Item 1-5. The polypeptide according to any one of Item 1 and Items (1-1) to (1-4), wherein the N-terminal region of βCTF comprises the amino acid sequence represented by SEQ ID NO: 15.

Item 1-6. The polypeptide according to any one of Item 1 and Items (1-1) to (1-5), wherein the binding satisfies the KD values of 50 μM or less.

Item 2. A γ-secretase activity inhibitor comprising the polypeptide according to any one of Item 1 and Items (1-1) to (1-6).

The inventions also include the embodiments described in Item 2-1 to Item 2-3 below.

Item 2-1. A βCTF-specific γ-secretase activity inhibitor comprising a polypeptide of any one of Item 1 and Item 1-1 to Item 1-6.

Item 2-2. The γ-secretase activity inhibitor according to Item 2, which comprises a polypeptide having the amino acid sequence represented by SEQ ID NO: 3.

Item 2-3. The βCTF-specific γ-secretase activity inhibitor according to Item 2, which comprises the amino acid sequence represented by SEQ ID NO: 3.

Item 3. A β-secretase activity inhibitor comprising a polypeptide of any one of Item 1 and Item 1-1 to Item 1-6.

The inventions further include the embodiments described in Item 3-1 to Item 3-3 below.

Item 3-1. An APP-specific β-secretase activity inhibitor comprising a polypeptide of any one of Item 1 and Item 1-1 to Item 1-6.

Item 3-2. The β-secretase activity inhibitor according to Item 3, which comprises a polypeptide having the amino acid sequence represented by SEQ ID NO: 6.

Item 3-3. The APP-specific β-secretase activity inhibitor according to Item 3, which comprises a polypeptide having the amino acid sequence represented by SEQ ID NO: 6.

Item 4. An Aβ protein production inhibitor comprising a polypeptide of any one of Item 1 and Item 1-1 to Item 1-6.

The inventions further include the embodiments described in Item 4-1 to Item 4-3 below.

Item 4-1. The Aβ-protein-specific production inhibitor comprising a polypeptide of any one of Item 1 and Item 1-1 to Item 1-6.

Item 4-2. The Aβ protein production inhibitor according to Item 4, which comprises a polypeptide having the amino acid sequence represented by SEQ ID NO: 6.

Item 4-3. The Aβ-protein-specific production inhibitor according to Item 4, which comprises a polypeptide having the amino acid sequence represented by SEQ ID NO: 6.

Item 5. An agent for treating and/or preventing Alzheimer's disease comprising a polypeptide of any one of Item 1 and Item 1-1 to Item 1-6.

The inventions further include the embodiment described in Item 5-1 below.

Item 5-1. The treatment and/or prevention agent according to Item 5, the agent comprising a polypeptide having the amino acid sequence represented by SEQ ID NO: 6.

Item 6. A method for treating and/or preventing Alzheimer's disease comprising administering the polypeptide of any one of Item 1 and Item 1-1 to Item 1-6 to an Alzheimer's disease patent.

The inventions further include the embodiment described in Item 6-1 below.

Item 6-1. The method according to Item 6, wherein a polypeptide having the amino acid sequence represented by SEQ ID NO: 6 is administered to an Alzheimer's disease patient.

Item 7. The polypeptide of any one of Item 1 and Item 1-1 to Item 1-6 for use in treating and/or preventing Alzheimer's disease.

The inventions further include the embodiment described in Item 7-1 below.

Item 7-1. The polypeptide of Item 7 having the amino acid sequence represented by SEQ ID NO: 6 for use in treating and/or preventing Alzheimer's disease.

Item 8. Use of the polypeptide of any one of Item 1 and Item 1-1 to Item 1-6 for use in manufacturing a pharmaceutical composition for treating and/or preventing Alzheimer's disease.

The inventions further include the embodiment described in Item 8-1 below.

Item 8-1. Use according to Item 8, wherein the polypeptide having the amino acid sequence represented by SEQ ID NO: 6 is used for manufacturing a pharmaceutical composition for treating and/or preventing Alzheimer's disease.

The present invention is explained in detail below.

A person skilled in the art can easily and reliably carry out the various techniques used in the present invention based on known documents and the like, except for techniques the source of which is particularly indicated. For example, in the fields of genetic engineering and molecular biological technology, the following documents may be referred to: Sambrook and Russell, "Molecular Cloning: A Laboratory Manual", Cold Spring Harbor Laboratory Press, New York (2001); Ausubel, F. M. et al.; "Current Protocols in Molecular Biology", John Wiley & Sons, New York.

Polypeptide

The polypeptide of the present invention has the amino acid sequence represented by any one of SEQ ID NOs: 1, 13, 14, and 22, preferably has the amino acid sequence represented by any one of SEQ ID NOs: 2-14 and 22, more preferably has the amino acid sequence represented by any one of SEQ ID NOs: 2-8, 10-12, 14, and 22, and further preferably has the amino acid sequence represented by any one of SEQ ID NOs: 3, 4, 6, 10, 11, 14, and 22.

In the amino acid sequence represented by SEQ ID NO: 1, the amino acid residue in the 2nd, 3rd, 4th, 5th, 11th, 12th, 13th, 14th, 16th, 19th, 21st, 22nd and 23rd positions are each one of the amino acid residues shown in Table 1 below

TABLE 1

| Position | Amino acid residues |
|---|---|
| 2 | Asn, Ser, Asp, Gly, His, Val, Leu, Arg, Phe |
| 3 | Thr, Ile, Leu, Pro, Tyr, Arg |
| 4 | Leu, Arg, Val, Ile, Thr, Phe, Ser |
| 5 | Ile, Val, Ser, Asp, Asn, Thr |
| 11 | Ser, His, Asp, Thr, Phe, Tyr, Ile, Ala |
| 12 | Leu, Gly, Asn, Ser, Thr, Ala, Arg, Tyr |
| 13 | Thr, Asp, Tyr, Ser, Phe, His, Asn |
| 14 | Arg, Leu, Val, Ala, Ile, Ser, Tyr |
| 16 | Phe, Tyr |
| 19 | Ser, Phe, Tyr |
| 21 | Val, Ile, Ser, Thr, Tyr, Gly, His, Arg |
| 22 | Asp, Asn, His, Pro, Ile, Arg, Ser |
| 23 | Ser, Val, Phe, Asn, Thr, Tyr, His, Ile, Arg, Asp |

The 3rd amino acid residue in the amino acid sequence represented by SEQ ID NO: 14 is L-4,4'-biphenylalanine residue. Particularly, in the polypeptide having the amino acid sequence represented by SEQ ID NO: 14, the carboxyl group of the 2nd glycine and the amide group in L-4,4'-biphenylalanine are linked together by a peptide bond, and the amide group of the 4th valine and the amide group of the L-4,4'-biphenylalanine are linked together by a peptide bond.

Likewise, the 3rd amino acid residue in the amino acid sequence represented by SEQ ID NO: 22 is L-4,4'-biphenylalanine residue. Particularly, in the polypeptide having the amino acid sequence represented by SEQ ID NO: 22, the carboxyl group of the 2nd arginine and the amide group in L-4,4'-biphenylalanine are linked together by a peptide bond, and the amide group of the 4th valine and the amide group of the L-4,4'-biphenylalanine are linked together by a peptide bond.

In the polypeptide of the present invention, an amide terminal may be acetylated or a carboxy terminal may be amidated. Furthermore, the amide terminal may be acetylated and the carboxy terminal may also be amidated.

The polypeptide of the present invention may be suitably modified. Examples of the modifications include, but are not limited to, biotin modification, fluorochrome modification, glycosilation, and lipid modification.

The modification sites are not particularly limited and may be the inside polypeptide, C-terminal of polypeptide, or N-terminal of polypeptide.

The modification method is not particularly limited, and a known method may be used.

The polypeptide of the present invention binds to the N-terminal region of βCTF. βCTF is a product of APP (e.g., a protein having the amino acid sequence of Accession No. Q95241.1 of NCBI, etc.) cleaved by β-secretase. Therefore, binding to the N-terminal region of βCTF is the same meaning as binding to the APP. Furthermore, the N-terminal region of βCTF corresponds to the region close to the cleavage recognition site by β-secretase on APP.

The region close to the N-terminal of βCTF can be recognized and cleaved also by γ-secretase. The fragment after the cleavage is produced as an Aβ protein (e.g., a protein having the amino acid sequence of Accession No 1Z0Q_A, 1BA6_A of NCBI); therefore, binding to the N-terminal region of βCTF is the same meaning as binding to the Aβ protein.

The amino acid sequence of the N-terminal region of βCTF to which the polypeptide of the present invention binds is not particularly limited. Examples include the amino acid sequence represented by SEQ ID NO: 15. Some of the amino acids of SEQ ID NO: 15 may also be given as examples. The N-terminal region of βCTF of the present invent does not necessarily contain Asp residue in the present invention at the N-terminal of βCTF.

Examples of the amino acid sequence of βCTF include, particularly in the case of human βCTF, the amino acid sequence represented by SEQ ID NO: 20. In the case of mouse βCTF, examples include the amino acid sequence represented by SEQ ID NO: 21.

The strength of the binding between the polypeptide of the present invention and the N-terminal region of βCTF is not particularly limited. If it is expressed, for example, by a dissociation constant (KD), it is generally in the range of 50 µM or less, and preferably about 5 µM or less.

The polypeptide of the present invention is soluble in various solvents without any limitation. Examples include solvents such as water, PBS, DMSO, and DMF. These solvents may be used in a combination of two or more.

The polypeptide of the present invention binds to the N-terminal region of βCTF. As explained above, this region corresponds to the region close to the γ-secretase cleavage recognition site on βCTF; therefore, it is useful as a γ-secretase activity inhibitor.

The polypeptide of the present invention binds to the N-terminal region of βCTF. As explained above, this region corresponds to the region close to the β-secretase cleavage recognition site on APP; therefore, it is useful as a β-secretase activity inhibitor.

The polypeptide of the present invention can be produced by using a known method. More particularly, a chemical production method using a peptide synthesizer or the like may be used, and a biochemical synthetic method may also be used, wherein a nucleic acid having a base sequence encoding the amino acid sequence of the polypeptide is introduced into a host cell.

The polypeptide of the present invention thus produced may be purified by using a known method such as using column chromatography.

γ-Secretase Activity Inhibitor

The γ-secretase activity inhibitor of the present invention contains the polypeptide of the present invention described above. Among the polypeptides described above, polypeptides having the amino acid sequence represented by any one of SEQ ID NOs: 2-14 and 22 are preferable.

Among the preferable polypeptides contained in the γ-secretase activity inhibitor of the present invention, polypeptides having the amino acid sequences represented by any one of SEQ ID NOs: 3, 4, 6, 7, 10, 14, and 22 are preferable.

Further examples of preferable polypeptides include those having the amino acid sequence represented by any one of SEQ ID NOs: 3, 4, 6, 10 and 14; polypeptides having the amino acid sequence represented by any one of SEQ ID NOs: 3, 4, 6, and 14; polypeptides having the amino acid sequence represented by any one of SEQ ID NOs: 3, 4, and 6; and polypeptides having the amino acid sequence represented by any one of SEQ ID NOs: 3 and 6 are preferable in increasing preference in this order. Among these, the most preferable is the polypeptide having the amino acid sequence represented by SEQ ID NO: 3.

As explained above, the polypeptide of the present invention contained in the γ-secretase activity inhibitor of the present invention binds to the N-terminal region of βCTF. The γ-secretase activity inhibitor of the present invention exhibits functions based on these phenomena. Therefore, in the present invention, there is a tendency that the γ-secretase activity towards the substrates other than βCTF recognized by the γ-secretase is not inhibited. More particularly, the γ-secretase of the present invention is preferably used as a βCTF-specific γ-secretase activity inhibitor.

The preferable "βCTF-specific" means that the γ-secretase activity inhibitor tends to select βCTF as the substrate for inhibiting its activity when βCTF and other substrate candidates for inhibiting the activity of γ-secretase are concurrently present.

When the γ-secretase activity inhibitor of the present invention is used as a βCTF-specific γ-secretase activity inhibitor, the γ-secretase activity inhibitor preferably exhibits competitive inhibition activity.

The γ-secretase activity inhibitor of the present invention contains the polypeptide of the present invention, and it may be used as a γ-secretase activity inhibitor without adding constituents other than the polypeptide.

When the γ-secretase activity inhibitor of the present invention contains constituents other than the polypeptide of the present invention, the constituents are not particularly limited as long as they do not adversely affect the γ-secretase activity inhibition effect, and known agents such as antiseptics, bactericides, and stabilizers may be contained. In this case, the content of the polypeptide of the present invention in the γ-secretase activity inhibitor of the present invention may be generally about 0.001 to 99.9 wt % relative to the weight of the γ-secretase activity inhibitor.

As described above, γ-secretase recognizes βCTF as a substrate and causes production of Aβ protein. Accordingly, the polypeptide of the present invention contained in the γ-secretase activity inhibitor of the present invention is also useful as an Aβ protein production inhibitor.

β-Secretase Activity Inhibitor

The β-secretase activity inhibitor of the present invention contains the polypeptide of the present invention described above. Among the polypeptides described above, polypeptides having the amino acid sequence represented by any one of SEQ ID NOs: 2-14 and 22 are preferable.

Among the preferable polypeptides contained in the β-secretase activity inhibitor of the present invention, polypeptides having the amino acid sequence represented by any one of SEQ ID NOs: 3-8, 10-12, 14, and 22 are preferable.

Further examples of preferable polypeptides include those having the amino acid sequence represented by any one of SEQ ID NOs: 3-8, 10, 12, and 14; polypeptides having the amino acid sequence represented by any one of SEQ ID NOs: 3-8, 12, and 14; polypeptides having the amino acid sequence represented by any one of SEQ ID NOs: 3-8 and 14; polypeptides having the amino acid sequence represented by any one of SEQ ID NOs: SEQ ID NOs: 3-6, 8, and 14; polypeptides having the amino acid sequence represented by any one of SEQ ID NOs: 3, 4, 6, 8, and 14; polypeptides having the amino acid sequence represented by any one of SEQ ID NOs: 3, 4, 6, and 8; polypeptides having the amino acid sequence represented by any one of SEQ ID NOs: 4, 6, and 8; and polypeptides having the amino acid sequence represented by any one of SEQ ID NOs: 4 and 6 are preferable in increasing preference in this order. Among these, the most preferable is the polypeptide having the amino acid sequence represented by SEQ ID NO: 4.

As explained above, the polypeptide of the present invention contained in the β-secretase activity inhibitor of the present invention binds to the recognition region close to the β-secretase cleavage recognition site on APP. The β-secretase activity inhibitor exhibits functions based on these phenomena. Therefore, in the present invention, there is a tendency that the β-secretase activity towards the substrates other than APP recognized by the β-secretase is not inhibited. More particularly, the β-secretase of the present invention is preferably used as an APP-specific β-secretase activity inhibitor.

The term "APP-specific" means that the β-secretase activity inhibitor tends to select APP as the substrate for inhibiting its activity when APP and other substrate candidates for inhibiting the activity of β-secretase are concurrently present.

When the β-secretase activity inhibitor of the present invention is used as an APP-specific β-secretase activity inhibitor, the β-secretase activity inhibitor preferably exhibits competitive inhibition activity.

The β-secretase activity inhibitor of the present invention contains the polypeptide of the present invention, and it may be used as a β-secretase activity inhibitor without adding constituents other than the polypeptide.

When the β-secretase activity inhibitor of the present invention contains constituents other than the polypeptide of the present invention, the constituents are not particularly limited as long as they do not adversely affect the β-secretase activity inhibition effect, and known agents such as antiseptics, bactericides, and stabilizers may be contained. In this case, the content of the polypeptide of the present invention in the β-secretase activity inhibitor of the present invention may be generally about 0.001 to 99.9 wt % relative to the weight of the γ-secretase activity inhibitor.

As described above, β-secretase recognizes APP as a substrate and causes production of βCTF. The produced βCTF is decomposed by the action of γ-secretase to produce Aβ protein. Accordingly, the polypeptide of the present invention contained in the β-secretase activity inhibitor of the present invention is also useful as an Aβ protein production inhibitor.

Aβ Protein Production Inhibitor

The Aβ protein production inhibitor of the present invention contains the polypeptide of the present invention described above. Among the polypeptides, polypeptides having the amino acid sequence represented by any one of SEQ ID NOs: 2-14 and 22 are preferable.

Among the preferable polypeptides contained in the Aβ protein production inhibitor of the present invention, polypeptides having the amino acid sequence represented by any one of SEQ ID NOs: 3, 4, 6, 10, 11, 14, and 22 are preferable.

Further examples of preferable polypeptides include those having the amino acid sequence represented by any one of SEQ ID NOs: 3, 4, 6, 10, 14, and 22; polypeptides having the amino acid sequence represented by any one of SEQ ID NOs: 3, 4, 6, 10, and 14; polypeptides having the amino acid sequence represented by any one of SEQ ID NOs: 3, 4, 6, and 14; polypeptides having the amino acid sequence represented by any one of SEQ ID NOs: 3, 4, or 6; polypeptides having the amino acid sequence represented by any one of SEQ ID NOs: 3 and 6 are preferable in increasing preference in this order. Among these, the most preferable is the polypeptide having the amino acid sequence represented by SEQ ID NO: 6.

The Aβ protein production inhibitor of the present invention contains the polypeptide of the present invention described above. The polypeptide, in particular, exhibits a βCTF-specific γ-secretase inhibition activation effect and/or APP-specific β-secretase activity inhibition effect. APP produces βCTF by the action of β-secretase, and βCTF produces Aβ protein by the action of γ-secretase. Therefore, the Aβ protein production inhibitor containing the polypeptide of the present invention exhibits the effect in particularly inhibiting the production of Aβ protein.

Thus, the Aβ protein production inhibitor is preferably used as an Aβ-protein-specific production inhibitor.

The term "Aβ-protein-specific" means that the Aβ protein production inhibitor of the present invention tends to selectively inhibit the production of Aβ protein when the Aβ protein coexists with other candidates for inhibiting production.

When the Aβ protein production inhibitor of the present invention contains constituents other than the polypeptide of the present invention, the constituents are not particularly limited as long as they do not adversely affect the Aβ protein production inhibition effect, and known agents such as antiseptics, bactericides, and stabilizers may be contained. In this case, the content of the polypeptide of the present invention in the Aβ protein production inhibitor of the present invention may be generally about 0.001 to 99.9 wt % relative to the weight of the Aβ protein production inhibitor.

Production and accumulation of Aβ protein is one of the pathogenic mechanisms of Alzheimer's disease; therefore, inhibiting production of Aβ protein is effective for prevention and/or treatment of Alzheimer's disease.

Accordingly, the polypeptide contained in the Aβ protein production inhibitor of the present invention is also useful as an agent for treating and/or preventing Alzheimer's disease.

For the reasons described above, the polypeptide of the present invention is suitably used for treating and/or preventing Alzheimer's disease.

For the specific uses in treating and/or preventing Alzheimer's disease, one may refer to the usage methods explained in detail in the section "Agent for Treating and/or Preventing Alzheimer's Disease" below.

The polypeptide of the present invention described above is suitably used for manufacturing a pharmaceutical composition for treating and/or preventing Alzheimer's disease.

For the specific uses for manufacturing medicine for treating and/or preventing Alzheimer's disease, one may refer to the usage methods explained in detail in the section below on treatment and/or prevention agent for Alzheimer's disease.

Agent for Treating and/or Preventing Alzheimer's Disease

The agent for treating and/or preventing Alzheimer's disease contains the polypeptide of the present invention described above. Among the polypeptides described above, polypeptides having the amino acid sequence represented by any one of SEQ ID NOs: 2-14, and 22 are preferable.

Among the preferable polypeptides contained in the agent for treating and/or preventing Alzheimer's disease of the present invention, polypeptides having the amino acid sequence represented by any one of SEQ ID NOs: 3, 4, 6, 10, 11, 14, and 22 are preferable.

Further examples of preferable polypeptides include those having the amino acid sequence represented by any one of SEQ ID NOs: 3, 4, 6, 10, 14, and 22; polypeptides having the amino acid sequence represented by any one of SEQ ID NOs: 3, 4, 6, 10, and 14; polypeptides having the amino acid sequence represented by any one of SEQ ID NOs: 3, 4, 6, and 14; polypeptides having the amino acid sequence represented by any one of SEQ ID NOs: 3, 4, and 6; and polypeptides having the amino acid sequence represented by any one of SEQ ID NOs: 3 and 6 are preferable in increasing preference in this order. Among these, the most preferable is the polypeptide having the amino acid sequence represented by SEQ ID NO: 6.

The agent for treating and/or preventing Alzheimer's disease contains the polypeptide of the present invention described above. In particular, the polypeptide exhibits an Aβ-protein-specific production inhibition effect. This allows the agent for treating and/or preventing Alzheimer's disease to achieve remarkable effects, such as few side effects.

When the agent for treating and/or preventing Alzheimer's disease of the present invention contains constituents other than the polypeptide of the present invention, the constituents may contain pharmacologically applicable carriers or additives as long as they do not adversely affect the effect of the agent for treating and/or preventing Alzheimer's disease.

Examples of pharmacologically applicable carriers or additives include any carriers, diluents, vehicles, suspensions, lubricants, adjuvants, media, emulsifiers, absorbents, preservatives, surfactants, colorants, flavoring agents, or sweeteners. Among these, any known may be used in a suitable manner.

In this case, the content of the polypeptide of the present invention in the agent for treating and/or preventing Alzheimer's disease of the present invention may be generally about 0.001 to 99.9 wt % relative to the weight of the agent for treating and/or preventing Alzheimer's disease.

The formulation of the agent for treating and/or preventing Alzheimer's disease of the present invention is not particularly limited and may be in a form of tablet, powder, syrup, poultice, injection, drops, or other form. Forming it into an injection or drops is preferable. The injection and drops may be aqueous, non-aqueous, or a suspension. The formulation may be a prepared when needed.

The agent for treating and/or preventing Alzheimer's disease of the present invention has potential for use in therapeutic procedures for treating immunologic diseases, comprising administering the agent to an Alzheimer's disease patient. The agent also has potential for use in prevention of Alzheimer's disease, comprising administering the agent to a patient who has not developed the pathology or symptoms of Alzheimer's disease but who may have predisposition to Alzheimer's disease. Furthermore, the agent also has potential to be used for a person who has mild cognitive impairment (e.g., MMSE of 26 or lower) in the preclinical stage of Alzheimer's disease.

In the present invention, there are no particular limitations to the Alzheimer's disease patients. For example, patients who have dysmnesia, disorientation, learning disability, attentional dysfunction, failures in spatial awareness function and problem-solving ability, and other disorders gradually progress and exhibit cognitive impairment and like symptoms. Observations in diagnostic imaging and the like include a patient diagnosed as having senile plaques (deposition image of Aβ protein) in the cerebral cortex observed, a patient diagnosed as having diffuse cerebral atrophy, and a patient diagnosed with tau protein, Aβ protein and like spinal fluid biomarkers, blood biomarkers, etc.

The dose and administration method of the agent for treating and/or preventing Alzheimer's disease of the present invention may be suitably selected in the range of 0.001 to 100 mg/kg/day depending on the patient's sex, race, age, general condition, severity of the disease, etc.

The agent for treating and/or preventing Alzheimer's disease of the present invention may be administered in the above doses once per day, or the dosage may be divided and administered several times. As long as the therapeutic effects can be achieved against the diseases mentioned above, the frequency of dosage may be once per day, every other day, every week, every other week, every two to three weeks, every month, every other month, or every two to three months. The administration route is not particularly limited, and the agent may be, for example, administered orally, intramuscularly, intravenously, intra-arterialy, intrathecaly, intradermaly, intraperitonealy, intranasaly, intrapulmonaryly, intraocularly, intravaginaly, intracervicaly, intrarectaly, and subcutaneously.

Method for Treating and/or Preventing Alzheimer's Disease

The method for treating and/or preventing Alzheimer's disease of the present invention comprises administering the polypeptide of the present invention to an Alzheimer's disease patient.

For the specific administration methods for Alzheimer's disease patients, refer to the methods described in detail in the section "Agent for Treating and/or Preventing Alzheimer's Disease" above.

Advantageous Effects of Invention

Examples of the effects of the polypeptide of the present invention are given below. The polypeptide of the present invention is, of course, not limited to those that have all of the effects mentioned below.

The polypeptide of the present invention is usable as an active ingredient of a γ-secretase activity inhibitor, in particular, a βCTF-specific γ-secretase activity inhibitor.

The polypeptide of the present invention is usable as an active ingredient of a β-secretase activity inhibitor, in particular, an APP-specific β-secretase activity inhibitor.

The polypeptide of the present invention is usable as an active ingredient of an Aβ protein production inhibitor, in particular, an Aβ-protein-specific production inhibitor.

The polypeptide of the present invention is usable as an active ingredient of an agent for treating and/or preventing Alzheimer's disease. In particular, when administered to an individual, such as a human, an agent for treating and/or preventing Alzheimer's disease with few side effect can be provided.

BRIEF DESCRIPTION OF DRAWINGS

FIG. 7-1 is a diagram showing the experimental results of FIG. 6 in the form of a graph.

FIG. 7-2 is a diagram showing the experimental results of FIG. 6 in a form of a graph.

FIG. 10(A) shows the results of an experiment wherein the biotinylated polypeptide of the present invention was reacted with CHO-K1 cells, and the cells were immobilized and treated with Triron X 100, and then reacted with avidin-modified Alexa 488. FIG. 10(B) shows the results of an experiment wherein the biotinylated polypeptide of the present invention was reacted with the CHO-K1 cells having overexpressed APP (hereunder referred to as "7WD10 cells"), and the cells were immobilized and treated with Triron X 100, and then reacted with avidin-modified Alexa 488. FIG. 10(C) shows the results of an experiment wherein 7WD10 cells were immobilized and treated with Triron X 100, and then reacted only with avidin-modified Alexa 488. In the figures, the bars indicate 50 µm.

FIG. 11(A) shows Western-blotting images wherein the polypeptide of the present invention was reacted with CHO-K1 cells and Neuro2A cells (N2A). FIG. 11(B) shows the results of analyzing the results of (A) with densitometry.

FIG. 12(A-1) and FIG. 12(A-2) show Western-blotting images analyzing the amounts of Aβ in the cerebral cortex after the administration into the abdominal cavity. FIG. 12(B) shows the results of analyzing the results of (A) with densitometry. FIG. 12(C) shows immunohistochemical stained images indicating the localization of the polypeptide of the present invention in the hippocampus after abdominal cavity administration. In the figures, the bars indicate 50 µm.

DESCRIPTION OF EMBODIMENTS

Figure 1:
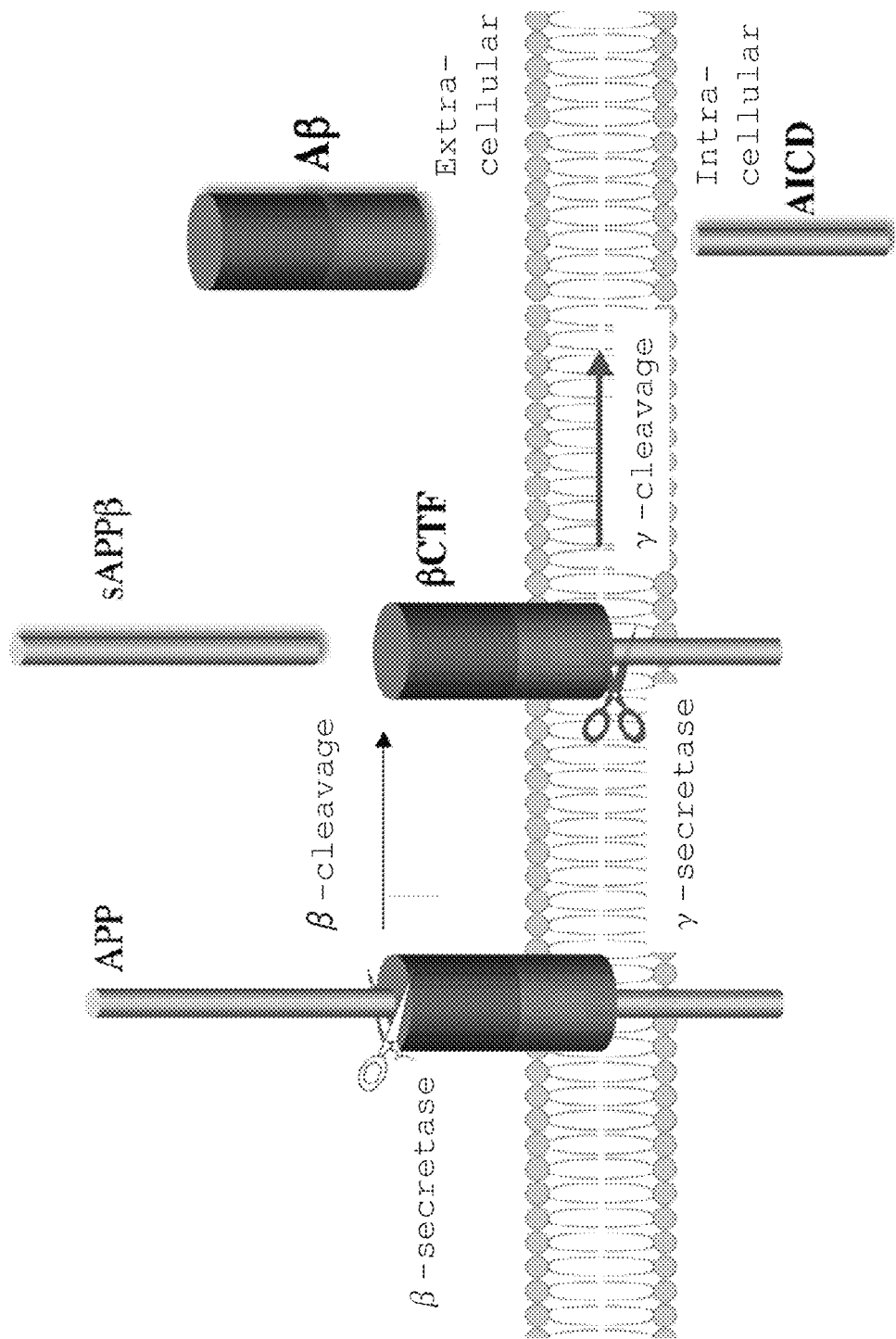
FIG. 1 is a schematic diagram showing the cleavage sites in Aβ protein, βCTF, APP, sAPPβ, and AICD cleaved by γ-secretase and β-secretase.

The Examples are described below for explaining the present invention in detail. The scope of the present invention is, of course, not limited to these Examples.

EXAMPLES

Production of Polypeptide

A polypeptide that specifically binds to polypeptide (Amyloid β 1-9), which is the polypeptide represented by SEQ ID NO: 15 corresponding to the N-terminal region of βCTF, was identified using the polypeptide screening technology.

TABLE 2

| Seq ID NO: | peptide name | amino acid sequence (N-terminus to C-terminus.) |
|---|---|---|
| 2 | 9-7 | MNTLICDCYCSLTRCFCYSCVDS |
| 3 | #1 | MSIRVCDCYCHGDLCFCYSCINS |
| 4 | #2 | MDTVICDCYCDNYVCFCYSCSHV |
| 5 | #3 | MGLISCDCYCDSTACFCYSCTDF |
| 6 | #4 | MHLVICDCYCTTDICYCYSCTPN |
| 7 | #5 | MVPVVCDCYCFLSVCFCYSCYIT |
| 8 | #6 | MLYTSCDCYCDAFSCFCYSCGPY |
| 9 | #7 | MRIFDCDCYCYRDICYCYFCTRH |
| 10 | #8 | MGRVNCDCYCIGHYCYCYYCHNI |
| 11 | #9 | MPLSICDCYCISTICYCYFCVHR |
| 12 | #10 | MPTVYCDCYCAYNACYCYYCRSD |
| 13 | 6-5 | MHHVYCDCYCFGPVCYCHSCT |
| 14 | S4 | FGBTWDYWVYR |
| 22 | S2 | FRBGWVYTYTV |
| 23 | L13 | MLICDCYCDPRSCICGSCTLV |

Note:
In the polypeptides, all the amino terminals are acetylated and the carboxy terminals are amidated. B in S4 (peptide name: SEQ ID NO. 14) and S2 (peptide name: SEQ ID NO. 22) is L-4,4'-biphenylalanine (Bph) residue.

In all the experiments below, the polypeptides having the amino acid sequences represented by SEQ ID NOs: 2-14 were all used in the state dissolved in DMSO.

The dissociation constant (KD) of peptide name "#4" having the amino acid sequence represented by SEQ ID NO: 15 described above was determined to be 2.62 µM.

In Vitro Analysis

Experimental Example 1

γ-Secretase Activity Inhibition Experiment 1

A polypeptide having βCTF (C99-FLAG: SEQ ID NO: 16) and mouse-derived Notch protein having a FLAG peptide at the C-terminal side (modification of NCBI Accession No. Q01705.2; SEQ ID NO: 17; hereunder referred to as "Notch") shown in FIG. 2(A) were each made into a solution having a final concentration of 50 nM.

To these solutions, 9-7 polypeptide, 6-5 polypeptide, #1 polypeptide, #2 polypeptide, #3 polypeptide, and #4 polypeptide were added in such a manner that the final concentrations were 50 µM, followed by reacting with 50 µL of CHAPSO-solubilized membrane fraction (γ-secretase-containing fraction) for 4 hours. The reaction temperature was 37° C. As a negative control experiment, DMSO was used in place of the six types of polypeptides described above.

Each sample after completion of the reaction was measured in the following manner. As shown in FIG. 2(A), a sample using C99-FLAG was subjected to Western blotting using a monoclonal antibody (82E-1) that specifically recognizes the N terminal of C99-FLAG, and the amount of Aβ40 protein produced by the cleavarage by γ-secretase was measured. In contrast, the reaction sample using Notch-FLAG was subjected to Western blotting using an anti-FLAG monoclonal antibody, and the amount of NICD produced to the separete by γ-secretase was also measured. FIG. 2(B) and FIG. 2(C) show the results.

FIG. 2(B) is a Western-blotting image indicating the presence of Aβ protein and NICD. In the image, a C99 band appears, indicating that C99-FLAG is barely separated by γ-secretase in the presence of the six polypeptides mentioned above. It became clear that, among the six polypeptides, #4, #2, #1, or like polypeptide inhibited more cleavage activity of γ-secretase against βCTF.

In contrast, in all the six polypeptides, bands indicating the presence of NICD appeared; therefore, it became clear that the cleavage activity of γ-secretase against Notch was not inhibited.

FIG. 2(C) is a graph wherein the Aβ protein and NICD were quantified based on the density of each band shown in the Western-blotting image of FIG. 2(B). In the graph, the vertical axis indicates the relative value taking the result of control using DMSO as 100%. It became clear that among the six polypeptides, in particular, #1 polypeptide inhibited the cleavage activity of γ-secretase against Aβ protein, but it did not inhibit the cleavage activity against Notch. This result suggests that #1 polypeptide most selectively inhibits the cleavage activity of γ-secretase against βCTF.

Experimental Example 2

γ-Secretase Activity Inhibition Experiment 2

An experiment was conducted in the same manner as in Experimental Example 1 described above, except that only #1 polypeptide was used and the amount of #1 polypeptide was selected so that the final concentrations were 0.5, 1, 5, 10, 20, and 50 µM.

Figure 3:
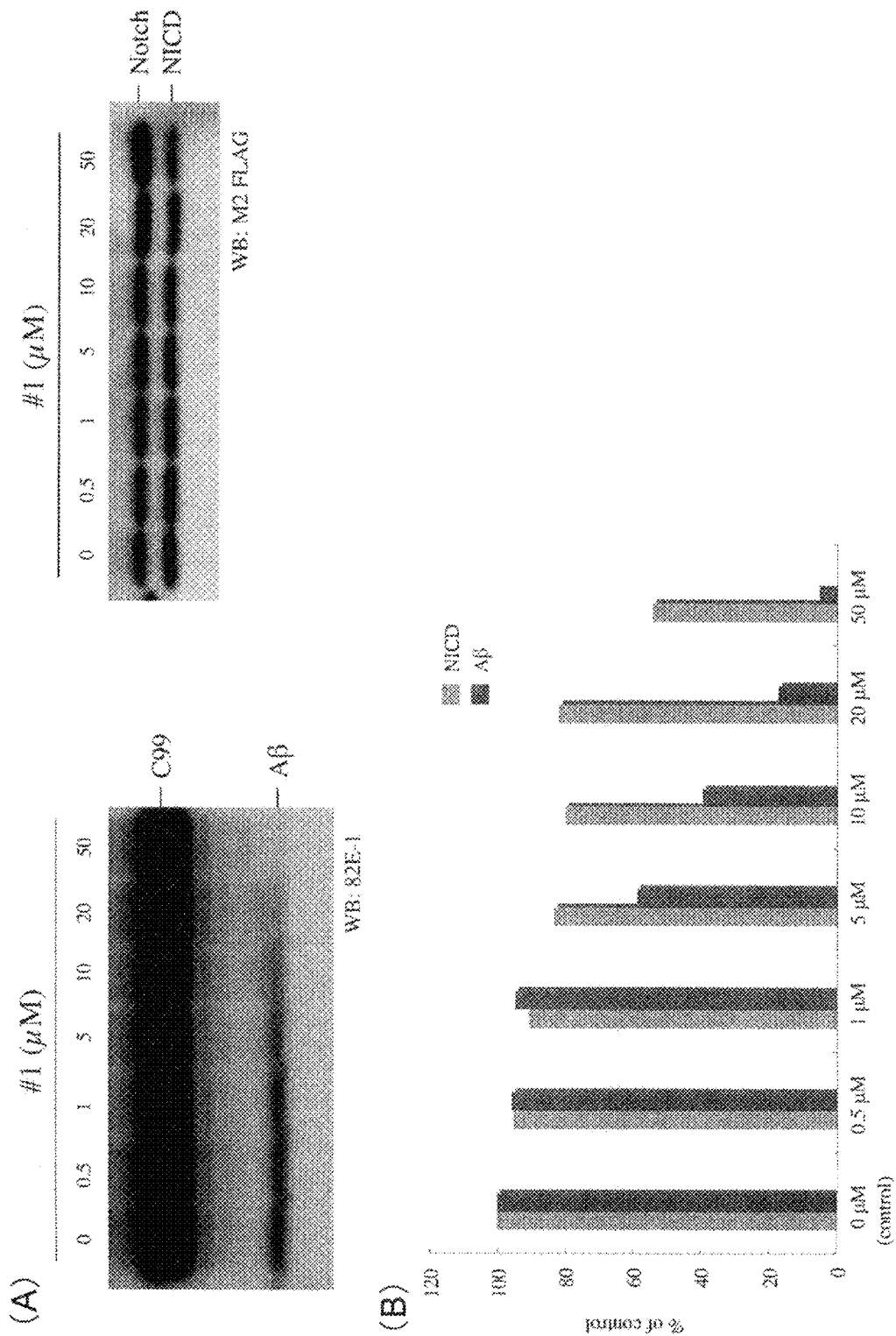
FIG. 3 is a diagram showing the results of the in vitro experiments of the polypeptide of the present invention in terms of the γ-secretase activity inhibition.

FIGS. 3(A) and 3(B) show the results. In the figures, 0 µM indicates the results of a negative control experiment wherein DMSO was used in place of #1 polypeptide. FIG. 3(A) is a Western-blotting image indicating the presence of Aβ protein and NICD. It became clear that #1 polypeptide more intensively inhibits the cleavage activity of γ-secretase against βCTF in a concentration-dependent manner.

However, regardless of the concentration of #1 polypeptide, a band indicating the presence of NICD appeared. Thus, it became clear that #1 polypeptide did not inhibit the cleavage activity of γ-secretase against Notch.

FIG. 3(B) is a graph wherein Aβ protein and NICD were quantified depending on the intensity of each band in the Western-blotting image shown in FIG. 3(A). In the graph, the vertical axis indicates the relative value taking the result of control using DMSO as 100%. It became clear that #1 polypeptide inhibited the cleavage activity of γ-secretase against βCTF in a concentration-dependent manner, but it did not inhibit the cleavage activity against Notch. This result suggests that #1 polypeptide most selectively inhibits the cleavage activity of γ-secretase against βCTF.

Experimental Example 3

γ-Secretase Activity Inhibition Experiment 3

An experiment was conducted in the same manner as in Experimental Example 1 described above, except that S4 polypeptide was used as the polypeptide, and each addition amount was set in such a manner that the final concentrations were 1, 5, 10, 20, and 50 µM. In this Experimental Example, #4 polypeptide was added in such a manner that the final result was 50 µM.

Figure 4:
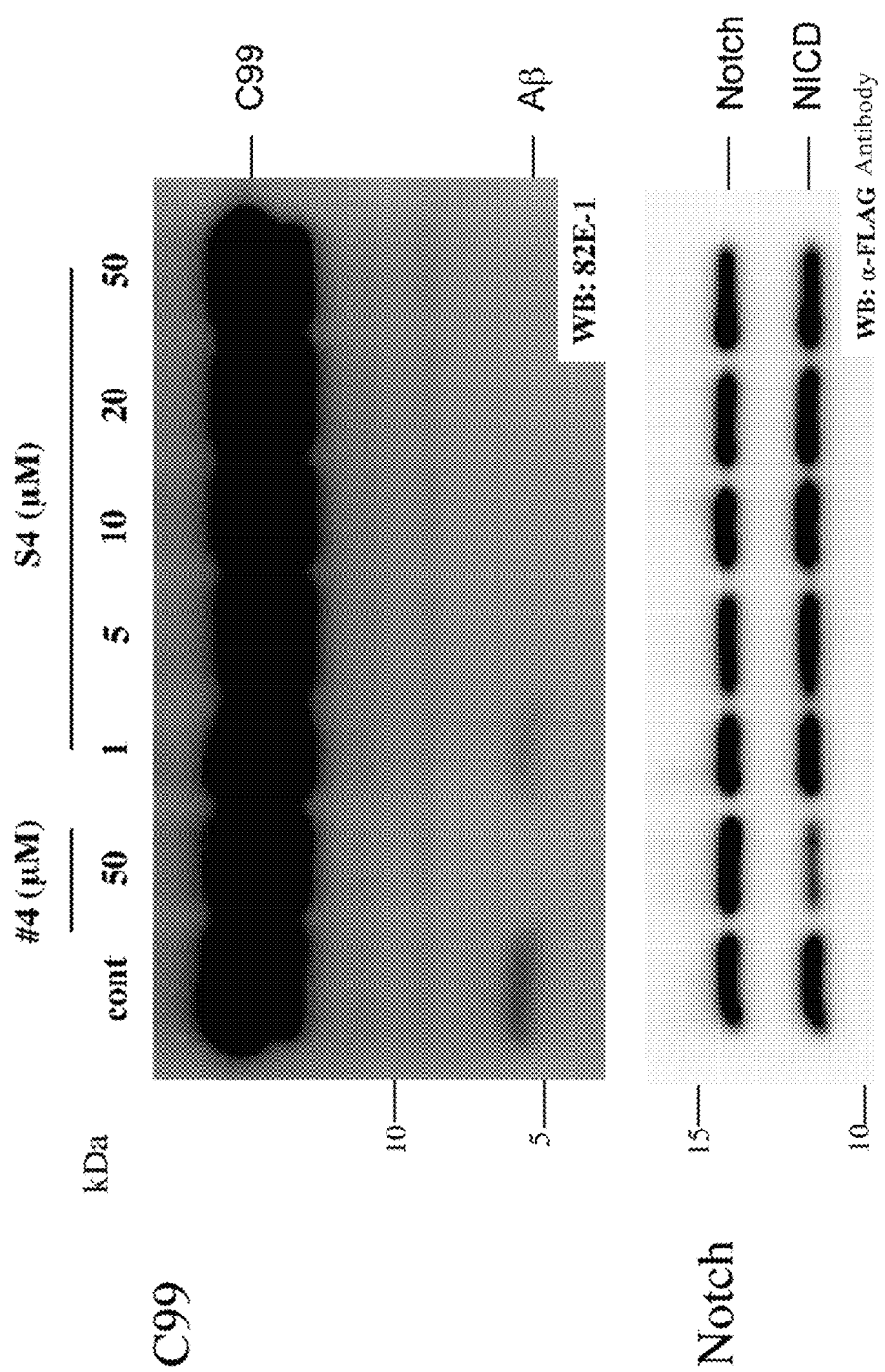
FIG. 4 is a diagram showing the results of the in vitro experiments of the polypeptide of the present invention in terms of the γ-secretase activity inhibition.

FIG. 4 shows the results. In the figure, "cont" indicates the negative control experiment wherein DMSO was used. FIG. 4 shows the Western-blotting image indicating the presence of Aβ protein and NICD. It became clear that as with #1 polypeptide, S4 polypeptide also inhibits more intensely in a concentration-dependent manner the cleavage activity of γ-secretase against βCTF.

As with #1 polypeptide, bands indicating the presence of NICD also appeared in the sample of S4 polypeptide regardless of the concentration. Therefore, it became clear that the cleavage activity of γ-secretase against Notch was not inhibited.

The above facts indicate that S4 polypeptide also selectively inhibits the cleavage activity of γ-secretase against βCTF, as with #1 polypeptide.

Experimental Example 4

β-Secretase Activity Inhibition Experiment 1

A solution containing the polypeptide having APP (APP-EQ-FLAG: SEQ ID NO: 18) as shown in FIG. 5(A) was prepared in such a manner that its final concentration was 50 nM.

To this solution, 9-7 polypeptide, 6-5 polypeptide, #1 polypeptide, #2 polypeptide, #3 polypeptide, #4 polypeptide, #5 polypeptide, #6 polypeptide, #7 polypeptide, #8 polypeptide, #9 polypeptide, and #10 polypeptide were added in such a manner that each solution had the final concentration of 50 µM, followed by reacting with 50 µL β-secretase (0.02 U/µL) for 4 hours. The reaction temperature was 37° C. As a negative control experiment, DMSO was used in place of the 12 types of polypeptides mentioned above.

Figure 5:
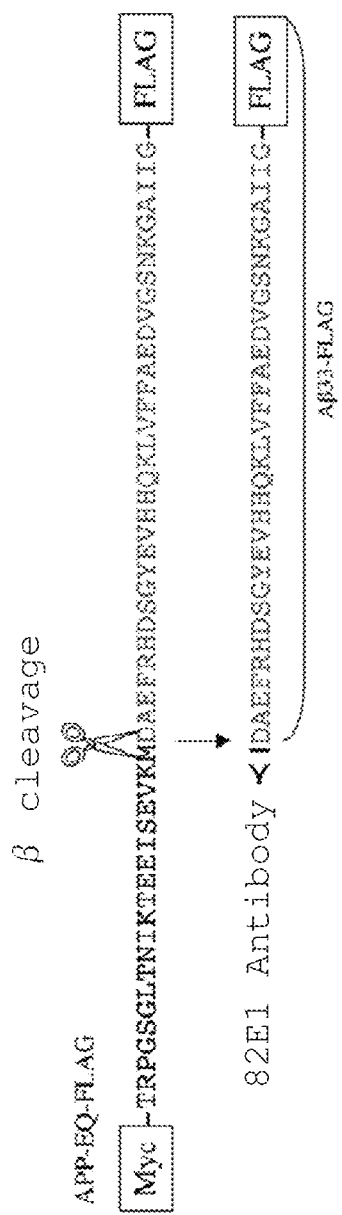
FIG. 5 is a diagram showing the results of the in vitro experiments of the polypeptide of the present invention in terms of the β-secretase activity inhibition. The upper amino acid sequence (APP-EQ-FLAG) corresponds to positions 12-72 of SEQ ID NO:18. The lower amino acid sequence (Aβ33-FLAG) corresponds to positions 32-72 of SEQ ID NO:18.
Figure 5:
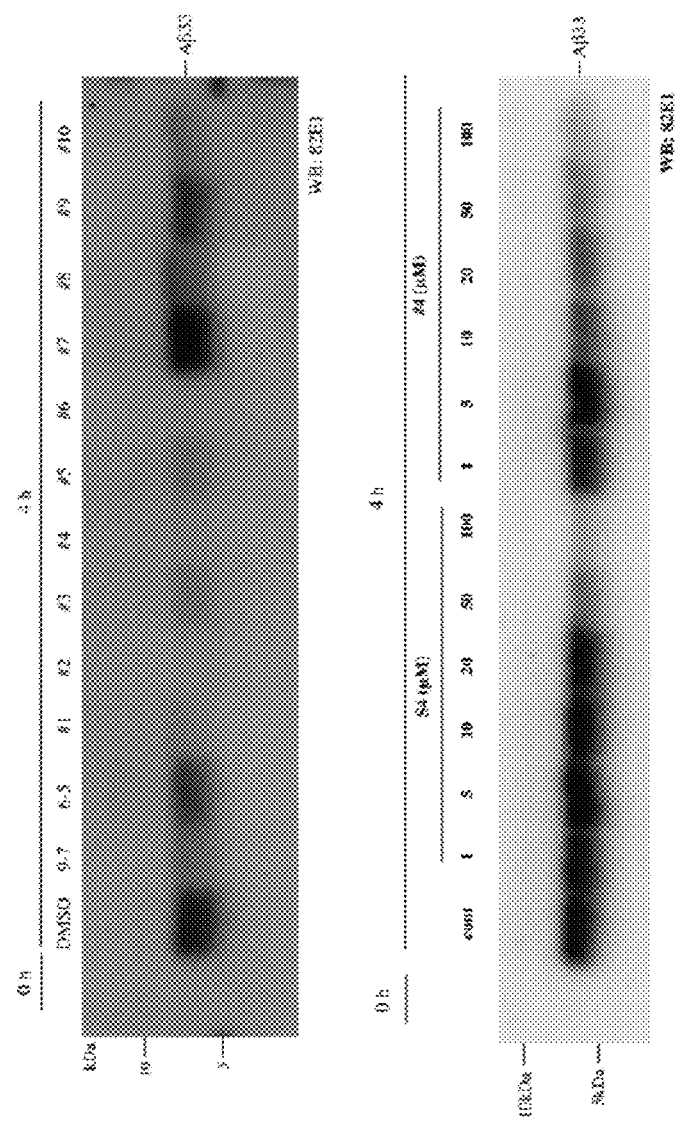

After completion of the reaction, each sample was subjected to Western blotting using a monoclonal antibody (82E-1) that specifically recognizes the N terminal of APP-EQ-FLAG as shown in FIG. 5(A). Thereafter, the amount of Aβ33-FLAG protein separated by β-secretase was measured.

FIG. 5(B) shows the results. FIG. 5(B) shows the Western-blotting image indicating the presence of βCTF (Aβ33). It became clear that, 11 types of polypeptides, except #7 polypeptide among the 12 types of polypeptides mentioned above, inhibit the cleavage activity of β-secretase against APP.

Among these, #2, #4, #6, #1, #3, #5, #10, #8, and #9 polypeptides preferably inhibit the cleavage activity of β-secretase against APP more intensely, with intensity increasing in this order.

Experimental Example 5

β-Secretase Activity Inhibition Experiment 2

An experiment was conducted in the same manner as Experimental Example 4 described above except that S4 and #4 polypeptides were used as the polypeptide and the amounts of these polypeptides added were adjusted so that the final concentrations were 1, 5, 10, 20, 50, and 100 μM.

FIG. 5(C) shows the results. In the figure, "cont" indicates the negative control experiment wherein DMSO was used.

It became clear that S4 polypeptide inhibited the cleavage activity of β-secretase against APP, although inferior to #4 polypeptide. It became clear that both S4 polypeptide and #4 polypeptide inhibited the cleavage activity of β-secretase against APP in a concentration-dependent manner more intensively than other polypeptides.

Analysis in Cultured Cells

Experimental Example 6

Aβ Protein Production Inhibition Experiment 1

An experiment was conducted wherein #1, #2, and #4 polypeptides were reacted with CHO-K1 cells (7WD10 cells) that stably expressed APP protein and transiently expressed Notch to confirm the production of Aβ protein and cleavage of Notch protein.

To culture medium of the above cells, three types of polypeptides were added in such a manner that each had a final concentration of 1, 5, 10, 20, and 50 μM. Thereafter, sAPPβ, NICD, βCTF (c99), and Aβ protein contained in the cell culture medium (Medium) or cell lysate were confirmed by using a Western-blotting method using antibodies for recognizing each (Aβ protein present in the cell lysate is referred to as "intracellular Aβ" and Aβ protein present in the cell culture medium is referred to as "released Aβ.").

FIG. 6, FIG. 7-1, and FIG. 7-2 show the results. In the figures, 1 μM L685458 shows the results of the experiment wherein L685458 (i.e., a γ-secretase inhibitor) was added in such a manner to have a final concentration of 1 μM in place of the three types of polypeptides described above.

Figure 6:
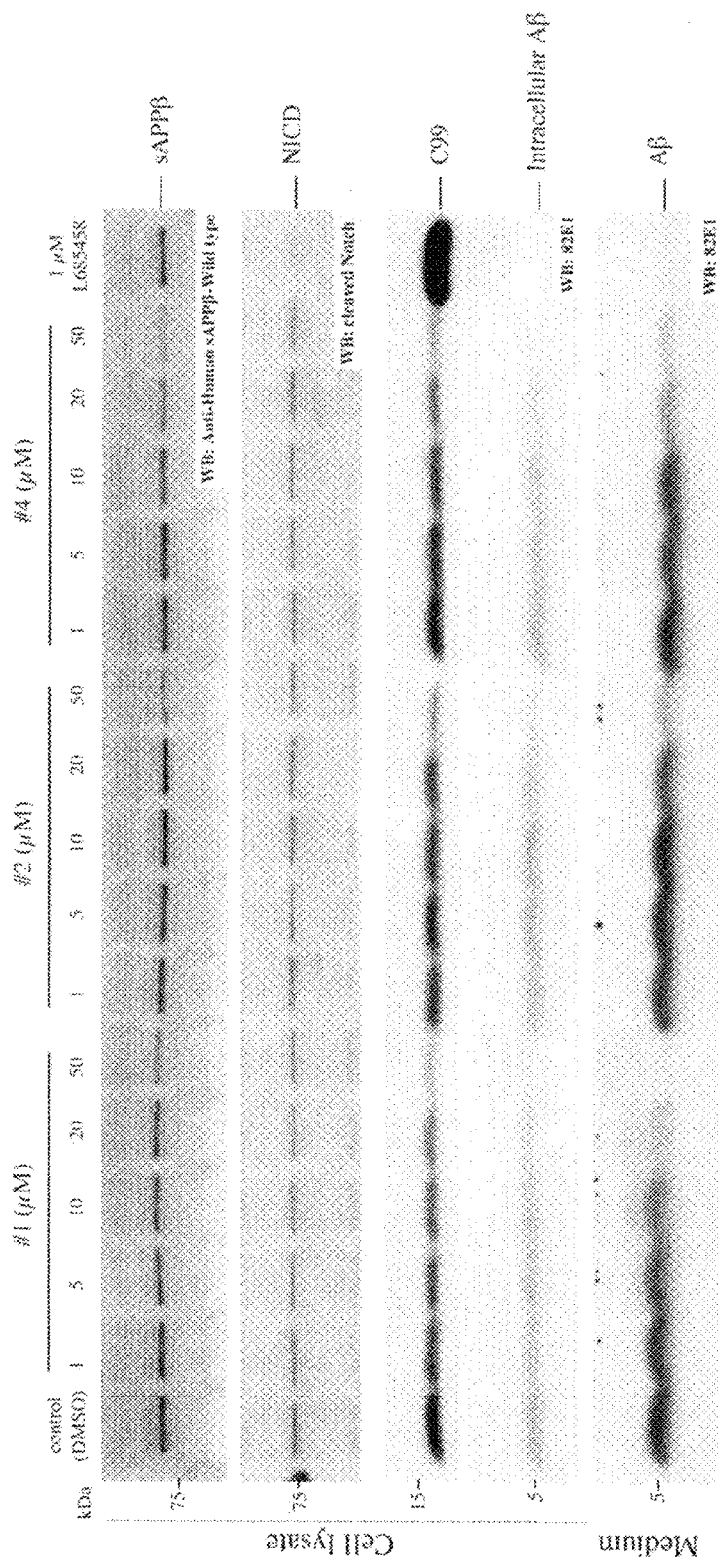
FIG. 6 is a diagram showing the results of the in vitro experiments of the polypeptide of the present invention in terms of the γ-secretase activity inhibition at the cellular level, β-secretase activity inhibition, and Aβ protein production inhibition.

FIG. 6 indicates that whenever #1, #2, or #4 polypeptide was added, sAPP in the cell lysate was no longer present in a manner dependent on the final concentration. This indicates that #1, #2, and #4 polypeptides all preferably inhibited the cleavage activity against APP expressing in the 7WD10 cells by internal β-secretase. In contrast, such a phenomenon was not observed when L685458 (i.e., a γ-secretase inhibitor) was used.

FIG. 6 indicates that whenever #1, #2, or #4 polypeptide was added, βCTF (C99) and Aβ protein in the cell lysate were no longer present in a manner dependent on the final concentration. As is evident from these facts, #1, #2, and #4 polypeptides all desirably inhibit the cleavage activity of the internal γ-secretase against the βCTF expressed in 7WD10 cells and the βCTF formed due to cleavage of APP by β-secretase. Such a phenomenon of decrease in βCTF (C99) and Aβ protein was also observed when L685458 (i.e., a γ-secretase inhibitor) was added.

Whenever #1, #2, or #4 polypeptide was added, Aβ protein in the cell culture medium also decreased depending on the concentration as used here. It also revealed that when L685458 was added, Aβ protein in the cell culture medium decreased.

The facts described above revealed that #1, #2, and #4 polypeptides all desirably inhibit the cleavage activity of the internal γ-secretase and β-secretase in cells having overexpression of APP. This indicates that #1, #2, and #4 polypeptides all inhibit the production of Aβ protein at the cellular level.

The results of the experiments clearly indicate that when #1, #2, and #4 polypeptides all were added, regardless of the concentrations of each, the abundance of the NICD in the cell lysate was not decreased. The results also clearly indicated that when L685458 (i.e., a γ-secretase inhibitor) was added, the amount of NICD was decreased.

These facts prove that #1, #2, and #4 polypeptides all specifically inhibit the cleavage activity of β-secretase against APP and the inhibition activity of γ-secretase against βCTF at the cellular level. These facts further indicate that these polypeptides have an activity that specifically inhibits the production of Aβ protein at the cellular level.

Figure 2:
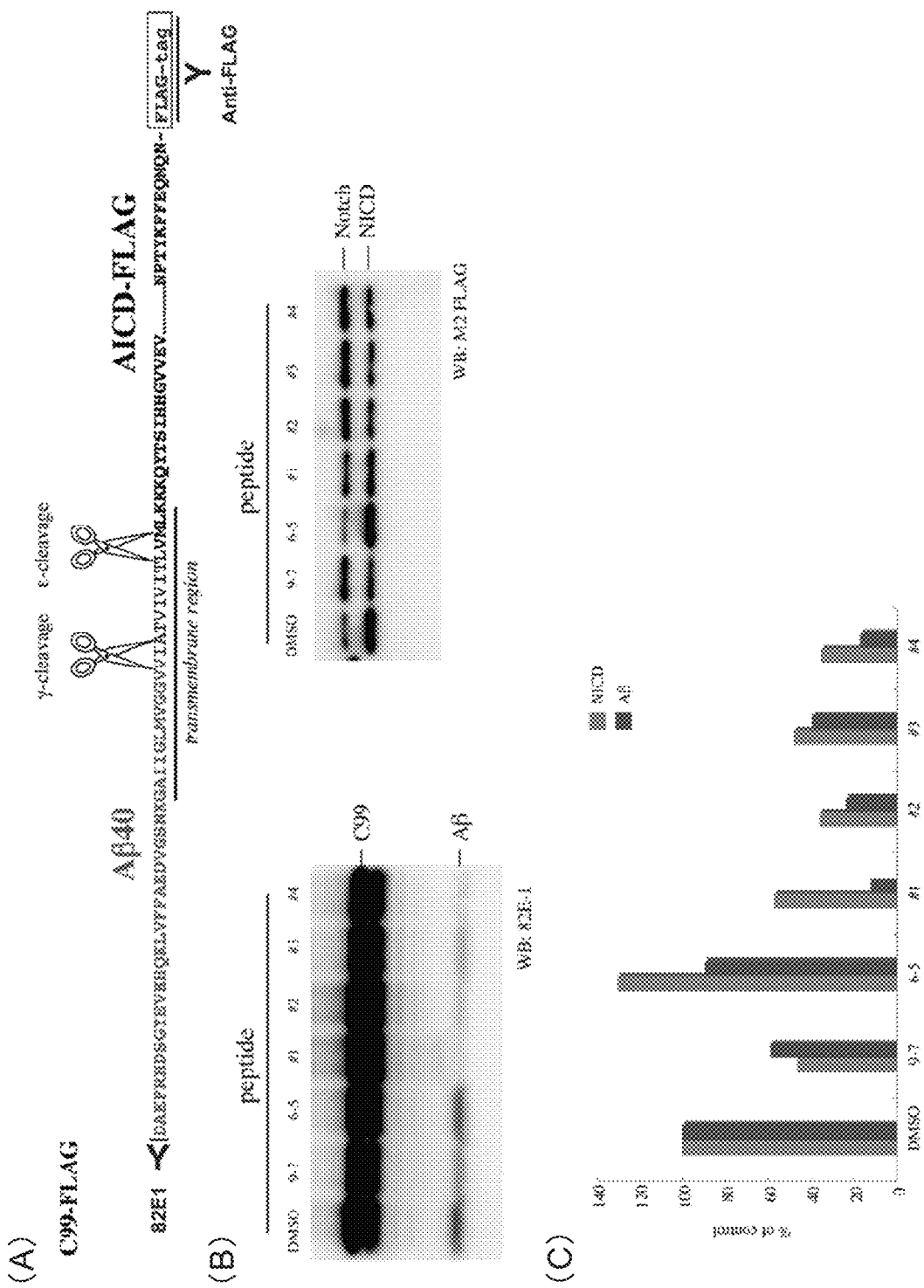
FIG. 2 is a diagram showing the results of the in vitro experiments of the polypeptide of the present invention in terms of the γ-secretase activity inhibition. The amino acid sequence (C99-FLAG) is set forth in SEQ ID NO: 16.
Figures 1, 7:
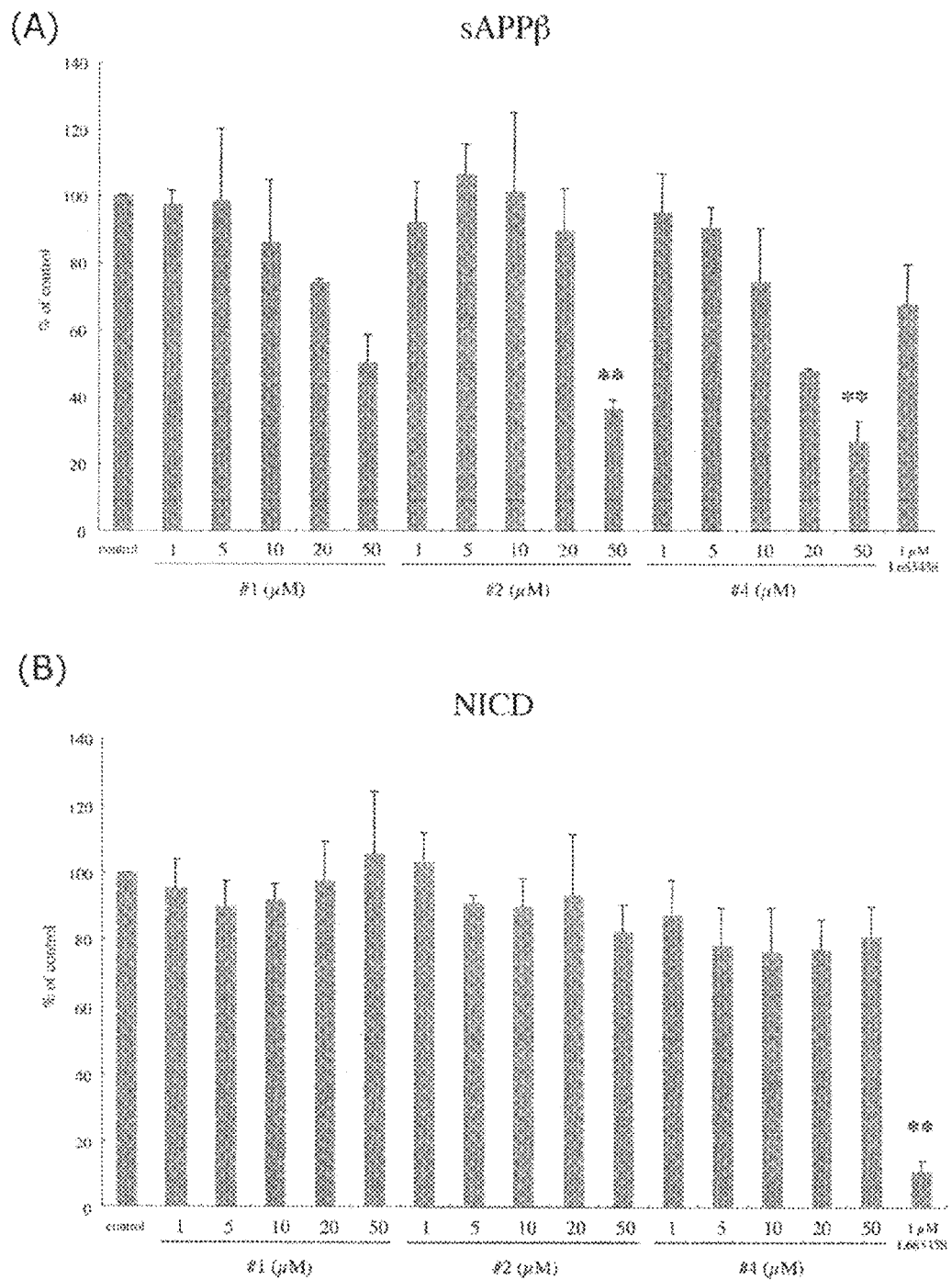
Figures 2, 7:
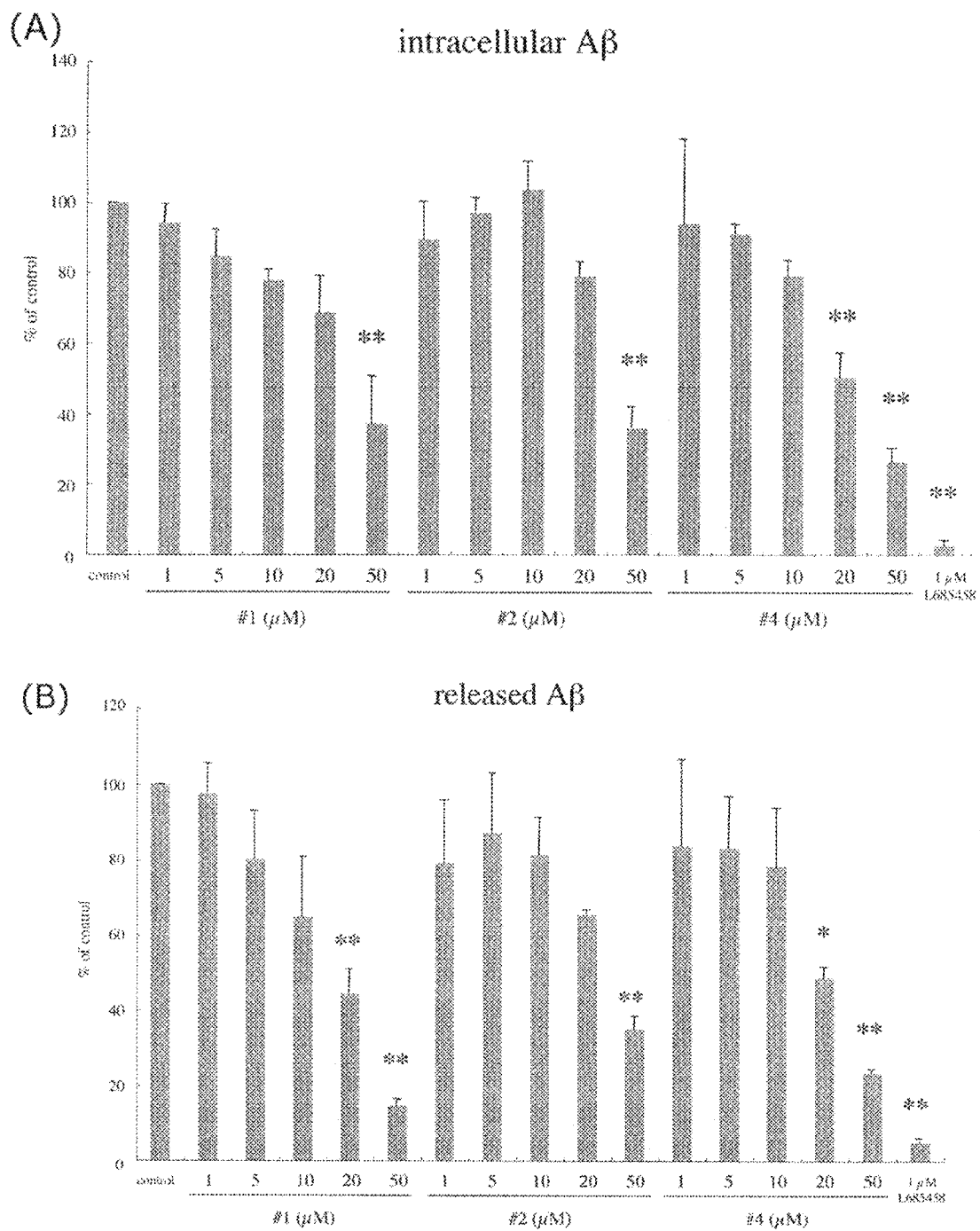

FIG. 7-1 and FIG. 7-2 are graphs where the amounts of sAPPβ, NICD, and Aβ protein in the cell lysate were quantified based on the intensity of each band in the Western-blotting image of FIG. 6. The vertical axis indicates the relative value taking the result of control using DMSO as 100%. Furthermore, the symbols "*" and "**" in the graphs respectively mean that there was a significant difference of $P<0.05$ and $p<0001$ in the ANOVA Scheffe's post hoc test.

The graphs of FIG. 7-1 and FIG. 7-2 also clearly show that, unlike L685458 (i.e., a γ-secretase inhibitor), #1, #2, and #4 polypeptides all specifically inhibit, at the cellular level, the cleavage activity of β-secretase against APP, and cleavage activity of γ-secretase against βCTF. Accordingly, at the cellular level, they specifically inhibit the production of Aβ protein.

Experimental Example 7

Aβ Protein Production Inhibition Experiment 2

An experiment was conducted in the same manner as Experimental Example 6 except that only S4 polypeptide was used as the polypeptide; the S4 polypeptide was added to have the final concentrations of 25 μM and 50 μM; the cell used in this experiment was CHO-K1 cell (7WD10 cell) that expressed APP protein and transiently expressed Notch and sialyltransferase (st6gal), which is the substrate of β-secretase; and confirmation of cleavage by sialyltransferase was conducted in addition to the confirmation of the production of Aβ protein and cleavage of Notch protein.

Figure 8:
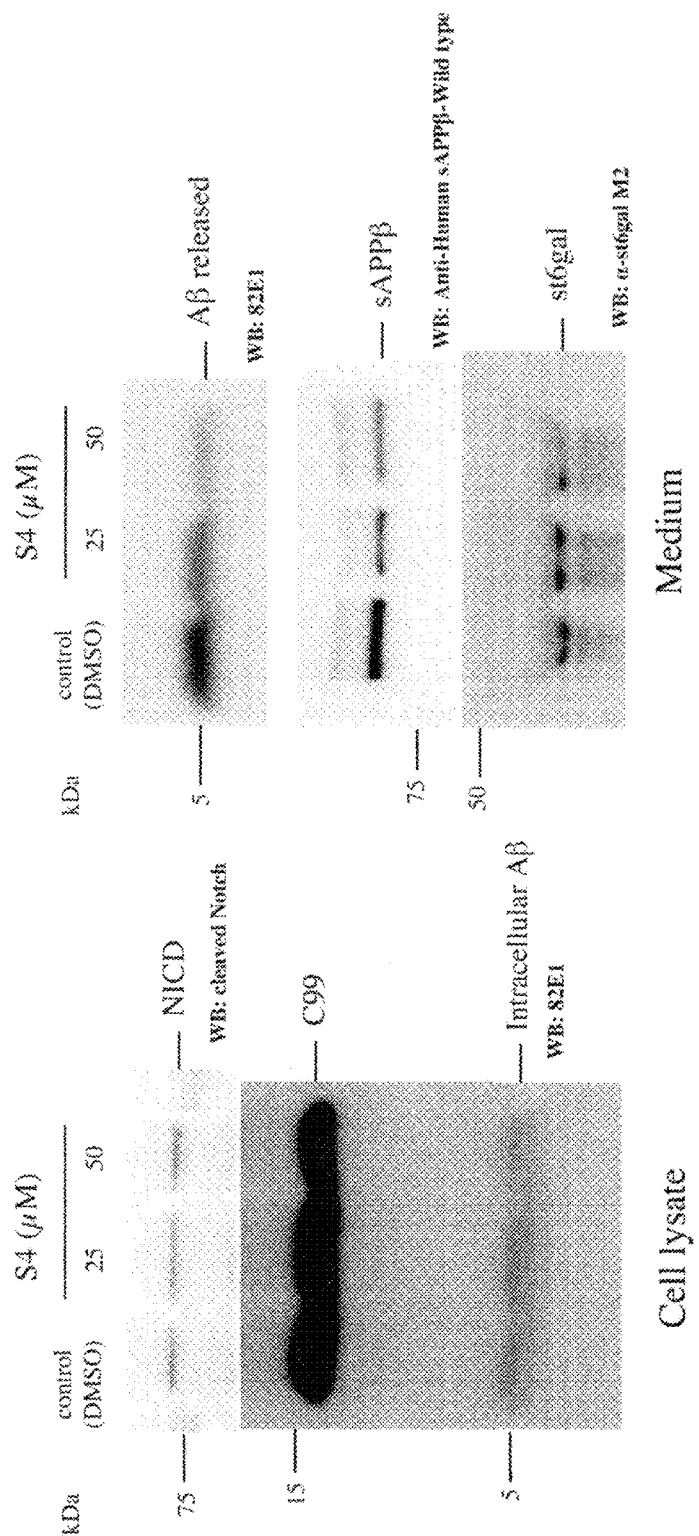
FIG. 8 is a diagram showing the results of the in vitro experiments of the polypeptide of the present invention in terms of the γ-secretase activity inhibition at the cellular level, β-secretase activity inhibition, and Aβ protein production inhibition.

FIG. 8 shows the results. It was revealed that when S4 polypeptide was added, Aβ protein (intracellular Aβ) in the cell lysate decreased, but the amount of NICD in the cell lysate did not decrease. This makes it clear that S4 polypeptide has γ-secretase inhibition activity even at the cellular level, and therefore specifically inhibits the cleavage activity of γ-secretase against βCTF.

When S4 polypeptide was added, the sAPPβ production amount in the cell culture medium was reduced, but the st6gal production amount in the cell culture medium was not decreased. This indicates that S4 polypeptide has β-secretase inhibition activity even at the cellular level, and therefore S4 polypeptide specifically inhibits the cleavage activity of β-secretase against APP.

It was also revealed that when S4 polypeptide was added, the amount of Aβ protein (released Aβ) in the cell culture medium was reduced. The above facts indicate that S4 polypeptide, as with #1, #2, and #4 polypeptide, has an activity that specifically inhibits the production of Aβ protein even at the cellular level.

Administration to Animals

Experimental Example 8

Aβ Protein Production Inhibition Experiment

A #4 polypeptide solution using 50% DMSO as a solvent was administered to a C57BL/6 mouse in an amount of 0.2 ng/g. The solution was directly administered in the right-side hippocampus of the mouse. Three hours after administration, the right-side hippocampus was extracted, and the amount of Aβ protein extracted by TBS and 6M guanidine hydrochloride was measured by using the sandwich ELISA method (product name: human/rat β amyloid (40) ELISA Kit Wako for immunochemistry, product No. 294-62501; product name: human/rat β amyloid (42) ELISA Kit Wako for immunochemistry, product No. 290-62501: both manufactured by Wako Pure Chemical Industries, Ltd.). As a negative control experiment, a polypeptide (rev#4: SEQ ID NO: 19) having the amino acid sequence in inverse order of #4 polypeptide was administered to the left-side hippocampus of the same mouse.

Figure 9:
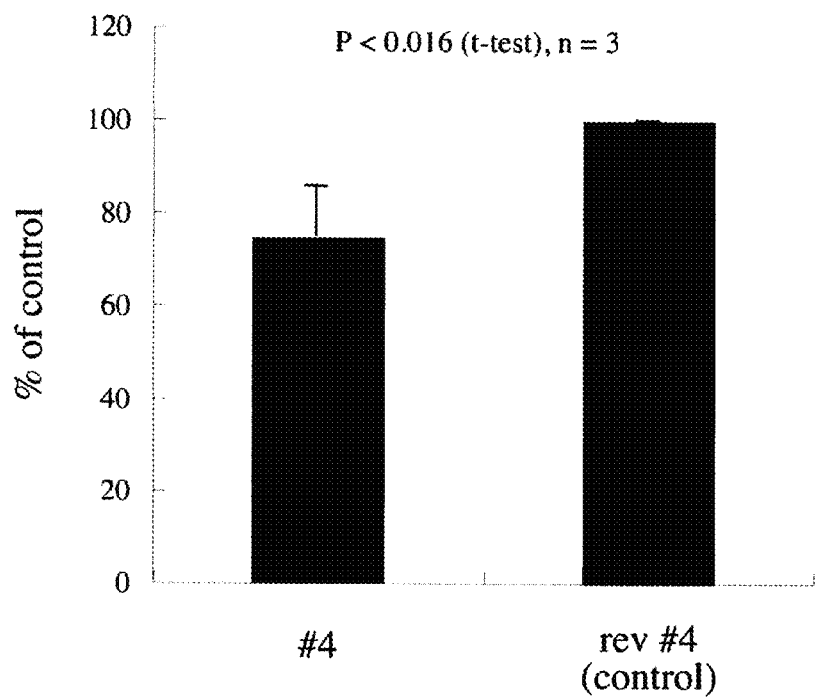
FIG. 9 is a diagram showing the experimental results of administering the polypeptide of the present invention to animal individual.

FIG. 9 shows the results. FIG. 9 is a graph showing the Aβ protein extracted from the mouse was quantified. The vertical axis indicates the relative value taking the result of negative control experiment in which rev#4 polypeptide was administered as 100%.

It was revealed that #4 polypeptide remarkably inhibited Aβ protein production even when administered to an individual mouse, as with the results of Experimental Example 6 described above. From these results, it can be expected that when any one of #1, #2, and S4 polypeptide is administered, Aβ protein production can be remarkably inhibited, as with #4 polypeptide.

Analysis in Cultured Cell: Part 2

Experimental Example 9

Analysis of Subcellular Distribution

Figure 10:
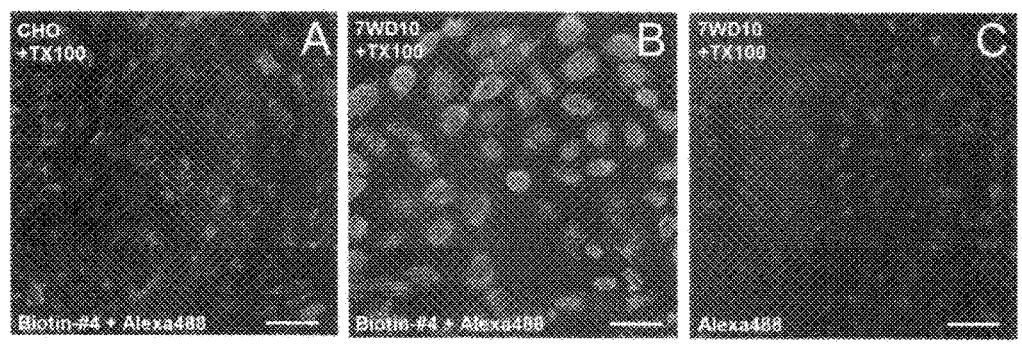
FIG. 10 is a figure showing the subcellular distribution of the polypeptide of the present invention.

Biotin-modified #4 polypeptide was prepared using a known method. This polypeptide was allowed to react with CHO-K1 cells and the 7WD10 cells mentioned above, and the resulting cells were immobilized, and then treated with Triton X-100. Thereafter, avidin-modified Alexa488 was reacted with the above. As the negative control experiment, an experiment was conducted reacting avidin-modified Alexa 488 in place of Biotin-modified #4 polypeptide. FIG. 10 shows the results. The experiment revealed that, in the CHO-K1 cells expressing endogenous APP protein at a low level, #4 polypeptide binded to APP in the cells. Furthermore, in 7WD10 cells overexpressing APP, #4 polypeptide remarkably binded also to the intracellular APP.

These results revealed that #4 polypeptide has a mechanism entering the cells and binding also to the APP before being exposed to the cell surface. This suggests that production of Aβ will be inhibited as a result.

Experimental Example 10

Mouse Aβ Production Inhibition Experiment

1, #2, and #4 polypeptides were added to the culture solutions of CHO-K1 cells and Neuro 2A cells (N2A) in such a manner that the final concentration was 20 μM. As a control, L685458 (i.e., a γ-secretase inhibitor) and DMSO were added thereto in such a manner that the final concentration was 20 μM.

Figure 11:
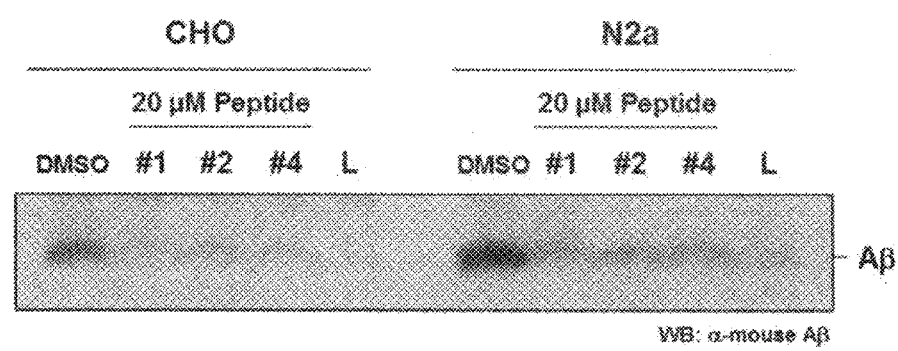
FIG. 11 is a figure showing the mouse-type Aβ production inhibition action of the polypeptide of the present invention.
Figure 11:
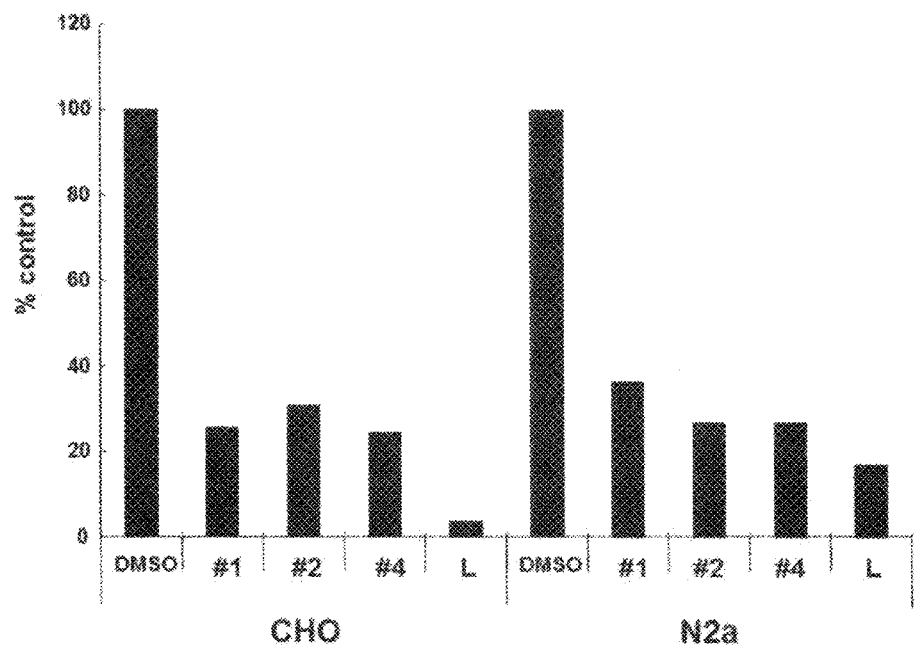

Thereafter, Aβ contained in the cell culture medium was identified by using a Western-blotting method with an antibody (anti-mouse Aβ antibody) that recognizes Aβ. FIG. 11 shows the results. In the figure, L indicates L685458, which is a γ-secretase inhibitor (final concentration of 1 μM). This figure shows that whenever any one of #1, #2, and #4 polypeptides was administered, the production of Aβ in the culture medium was reduced also against CHO-K1 and Neuro2A cells. Both CHO-K1 cells and Neuro2A cells express mouse-type APP; therefore, #1, #2, and #4 polypeptides all clearly inhibit production of mouse-type Aβ protein.

Administration to Animals

Part 2

Experimental Example 11

Intraperitoneal Administration to Mouse 150 mg/kg #4 polypeptide dissolved in DMSO was intraperitoneally administered to ten wild-type mice (C57 BL/6 N Cr Slc, seven weeks old). The administration was conducted for three consecutive days. Four days after, the mice were euthanized to extract the cerebrum.

The extracted cerebrums were dissolved by using a known method, subjected to immunoprecipitation with anti-4G8 antibody, and then subjected to Western blotting using the anti-mouse Aβ antibody. An experiment was conducted in the same manner except that only DMSO was administered as the negative control experiment group (ten mice).

Figure 12:
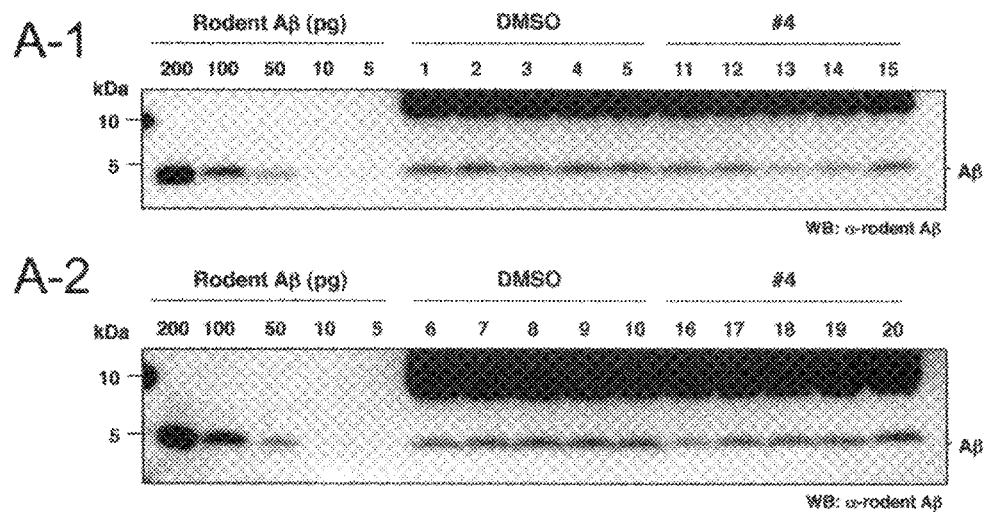
FIG. 12 is a figure showing the results of an experiment wherein the polypeptide of the present invention was administered into the mouse abdominal cavity.
Figure 12:
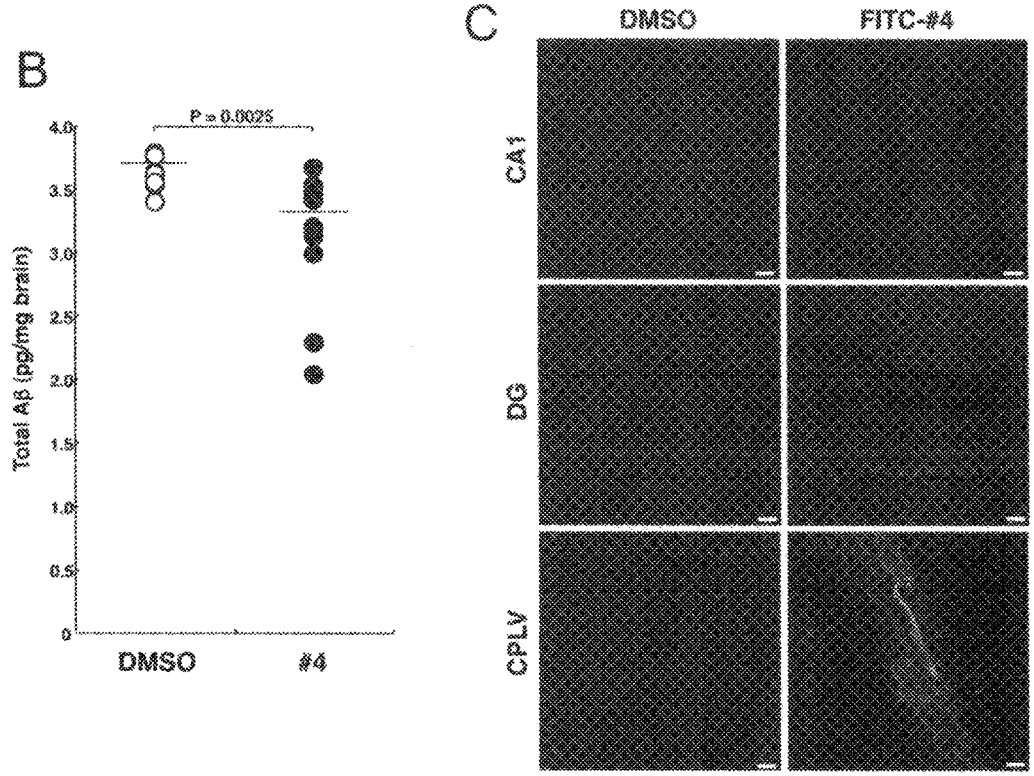

In the Western blotting, an experiment was conducted using 5, 10, 50, 100, and 200 pg rodent-originated Aβ as the standard reference material. FIG. 10(A–1) and FIG. 12(A-2) show the results.

It became clear that, compared to the bands of Aβ in the negative control experiments (1-5 and 6-10), the number of bands indicating Aβ was reduced in the cerebrum of mice to which #4 polypeptide was intraperitoneally administered. Furthermore, FIG. 12(B), which shows the results of quantifying these bands with densitometry, clearly indicates that #4 polypeptide exhibits an excellent Aβ production inhibition effect.

Subsequently, FITC-modified #4 polypeptide prepared by using a known method was intraperitoneally administered to a mouse. The dose was 150 mg/kg, and the administration was conducted for three consecutive days. Four days after, the mice were euthanized to prepare test pieces of tissue around the hippocampus. As the negative control experiment, DMSO was administered in place of FITC-modified #4 polypeptide. FIG. 12(C) shows the results of analyzing the test pieces using fluorescent microscopy.

In the figure, "CA1" indicates the area called the "CA1 region." Here, compared to the negative control experiment, a portion dyed green indicating the presence of #4 polypeptide was confirmed. In the figure, "DG" indicates the area called the "dentate gyrus," and a portion dyed green indicating the presence of #4 polypeptide was also confirmed in this portion. In the figure, "CPLV" indicates the area called the "choroid plex" for producing cerebrospinal fluid. In this area, a portion dyed green indicating the presence of #4 polypeptide was confirmed in the blood vessel.

Experimental Example 12

Aβ Protein Production Inhibition Experiment 3

An experiment was conducted in the same manner as in Experimental Example 6 by reacting #4, L13, S2, and S4 polypeptides with CHO-K1 cells (7WD10 cells) that stably express APP protein and transiently express Notch, followed by confirming the production of Aβ protein and cleavage of Notch protein.

To culture medium of the above cells, four types of polypeptides were added in such a manner that each had a final concentration of 25 or 50 μM as shown in the figure (#4 polypeptide had only 25 μM). Thereafter, the presence of Aβ protein contained in the cell culture medium (Medium) and NICD in the cell lysate were confirmed by using a Western-blotting method with antibodies for recognizing each.

Figure 13:
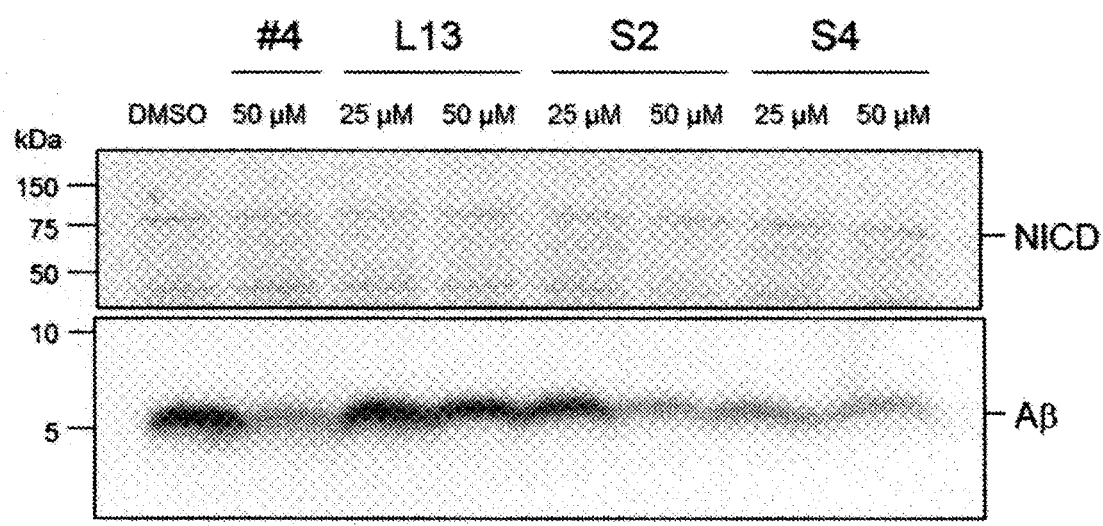
FIG. 13 is a figure showing the results of the Aβ protein production inhibition experiment of the polypeptide of the present invention.

FIG. 13 shows the results. In the figure, DMSO shows the results of the negative control.

FIG. 13 clearly shows that when S2 polypeptide was used in an amount having a final concentration of 50 μM, it exhibited the Aβ protein production inhibition effect almost to the same level as #4 polypeptide and S4 polypeptide. It did not have any influence on NICD. Accordingly, this figure indicates that S2 polypeptide also has an activity specifically inhibiting the production of Aβ protein.

In contrast, L13 polypeptide did not have any affect on NICD, but did not inhibit the production of Aβ.

The results described above reveal that the polypeptide of the present invention delivered to the brain even when intraperitoneally administered, and exhibits an effect inhibiting the production of Aβ in the brain. Furthermore, because it is clear that the polypeptide of the present invention inhibits production of not only mouse-type Aβ but also human Aβ, this suggests that the polypeptide of the present invention will also achieve the effect of inhibiting the production of Aβ in the brain when administered to a human.

SEQUENCE LISTING

PCT_amyloid β protein_20130116_102216_2.txt

The invention claimed is:

1. A polypeptide having the amino acid sequence of any one of SEQ ID NOs: 1, 13, 14, and 22 wherein the polypeptide binds to the N-terminal region of βCTF.

2. The polypeptide according to claim 1, wherein the polypeptide has the amino acid sequence of any one of SEQ ID NOs: 2-12.

3. The polypeptide according to claim 1, wherein the polypeptide has the amino acid sequence of any one of SEQ ID NOs: 2-8 and 10-12.

4. The polypeptide according to claim 1, wherein the polypeptide has the amino acid sequence of any one of SEQ ID NOs: 3, 4, 6, 10 and 11.

5. A γ-secretase activity inhibitor comprising a polypeptide of any one of claims 1 to 4.

6. A γ-secretase activity inhibitor comprising a polypeptide having the amino acid sequence of SEQ ID NO: 3.

7. A β-secretase activity inhibitor comprising a polypeptide of any one of claims 1 to 4.

8. A β-secretase activity inhibitor comprising a polypeptide having the amino acid sequence of SEQ ID NO: 6.

9. An Aβ protein production inhibitor comprising a polypeptide of any one of claims 1 to 4.

10. An Aβ protein production inhibitor comprising a polypeptide having the amino acid sequence of SEQ ID NO: 6.

11. A polypeptide having the amino acid sequence of SEQ ID NO: 13 wherein the polypeptide binds to the N-terminal region of βCTF.

12. A polypeptide having the amino acid sequence of SEQ ID NO: 14 wherein the polypeptide binds to the N-terminal region of βCTF.

13. A polypeptide having the amino acid sequence of SEQ ID NO: 22 wherein the polypeptide binds to the N-terminal region of βCTF.

14. A method for treating Alzheimer's disease in a subject in need thereof, comprising administration of a polypeptide of any one of claims 1 to 4 to the subject, thereby treating the subject.

15. A method for treating Alzheimer's disease in a subject in need thereof, comprising administration of a polypeptide having the amino acid sequence of SEQ ID NOs: 3, 4, 6, 14 or 22 to the subject, thereby treating the subject.

* * * * *